US010105413B2

(12) United States Patent
Vadasz et al.

(10) Patent No.: US 10,105,413 B2
(45) Date of Patent: Oct. 23, 2018

(54) SEMAPHORIN 3A FOR TREATMENT OF SYSTEMIC LUPUS ERYTHEMATOSUS

(71) Applicant: Medical Research & Development Fund for Health Services Bnai Zion Medical Center, Haifa (IL)

(72) Inventors: Zahava Vadasz, Haifa (IL); Elias Toubi, Haifa (IL)

(73) Assignee: Medical Research & Development Fund for Health Services Bnai Zion Medical Center, Haifa (IL)

( * ) Notice: Subject to any disclaimer, the term of this patent is extended or adjusted under 35 U.S.C. 154(b) by 0 days.

(21) Appl. No.: 14/897,061

(22) PCT Filed: Jun. 13, 2013

(86) PCT No.: PCT/IL2013/050504
§ 371 (c)(1),
(2) Date: Dec. 9, 2015

(87) PCT Pub. No.: WO2014/199364
PCT Pub. Date: Dec. 18, 2014

(65) Prior Publication Data
US 2016/0129079 A1    May 12, 2016

(51) Int. Cl.
*A61K 38/17* (2006.01)
*A61K 45/06* (2006.01)
*C07K 14/47* (2006.01)
*G01N 33/68* (2006.01)
*G01N 33/564* (2006.01)

(52) U.S. Cl.
CPC .......... *A61K 38/1709* (2013.01); *A61K 38/17* (2013.01); *A61K 38/1774* (2013.01); *A61K 45/06* (2013.01); *G01N 33/564* (2013.01); *G01N 33/68* (2013.01); *G01N 2333/4703* (2013.01); *G01N 2333/4716* (2013.01); *G01N 2800/104* (2013.01); *G01N 2800/52* (2013.01)

(58) Field of Classification Search
CPC ................ A61K 38/17; A61K 38/1709; A61K 38/1774; A61K 45/06; C07K 14/47
See application file for complete search history.

(56) References Cited

U.S. PATENT DOCUMENTS

| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 8,871,205 B2 * | 10/2014 | Ting ....................... C07K 16/28 424/134.1 |
| 2009/0324615 A1 | 12/2009 | Ting et al. |
| 2012/0251539 A1 * | 10/2012 | Ting ....................... C07K 16/28 424/134.1 |
| 2012/0322085 A1 * | 12/2012 | Kumanogoh .......... C07K 16/18 435/7.24 |
| 2015/0368327 A1 * | 12/2015 | Goshima ................ C07K 16/18 424/133.1 |

FOREIGN PATENT DOCUMENTS

| EP | 2 123 280 A1 | 11/2009 |
| WO | 2004/093647 A2 | 11/2004 |

OTHER PUBLICATIONS

Hayashi, M. et al. Osteoprotection by semaphorin 3A. Nature, 2012, vol. 485, p. 69-74).*
Acevedo et al., (2008) Semaphorin 3A suppresses VEGF-mediated angiogenesis yet acts as a vascular permeability factor. Blood 111(5): 2674-2680.
Ben-Zvi et al., (2006) Semaphorin 3A and neurotrophins: a balance between apoptosis and survival signaling in embryonic DRG neurons. J Neurochem 96(2): 585-597.
Bombardier et al., (1992) Derivation of the SLEDAI. A disease activity index for lupus patients. The Committee on Prognosis Studies in SLE. Arthritis Rheum 35(6): 630-640.
Capolunghi et al., (2010) Pharmacological inhibition of TLR9 activation blocks autoantibody production in human B cells from SLE patients. Rheumatology (Oxford) 49(12): 2281-2289.
Caruthers et al., (1987) Chemical synthesis of deoxyoligonucleotides by the phosphoramidite method. Methods Enzymol 154: 287-313.
Catalano (2010) The neuroimmune semaphorin-3A reduces inflammation and progression of experimental autoimmune arthritis. J Immunol 185(10): 6373-6383.
Catalano et al., (2006) Semaphorin-3A is expressed by tumor cells and alters T-cell signal transduction and function. Blood 107(8): 3321-3329.
Chakraborty et al., (2012) Semaphorin 3A suppresses tumor growth and metastasis in mice melanoma model. PLoS One 7(3): e33633, 13 pages.
Cooper et al., (2003) The epidemiology of autoimmune diseases. Autoimmun Rev 2(3): 119-125.
Dolff et al., (2011) Disturbed Th1, Th2, Th17 and Treg balance in patients with systemic lupus erythematosus. Clin Immunol 141(2): 197-204.
Eixarch et al., (2013) Semaphorins 3A and 7A: potential immune and neuroregenerative targets in multiple sclerosis. Trends Mol Med 19(3): 157-164.
Glinka et al., (2008) Neuropilin-1 is a receptor for transforming growth factor β-1, activates its latent form, and promotes regulatory T cell activity. J Leukoc Biol 84(1): 302-310.

(Continued)

Primary Examiner — Robert S Landsman
Assistant Examiner — Bruce D. Hissong
(74) Attorney, Agent, or Firm — Vorys, Sater, Seymour & Pease LLP

(57) ABSTRACT

The subject matter relates to Semaphorin 3A (Sema3A) and its use in treatment and prognosis of Systemic Lupus Erythematosus (SLE). Provided are, inter-alia, methods of treating a subject afflicted with SLE, comprising administering to the subject a pharmaceutical composition comprising isolated Sema3A. Further provided are methods for prognosis of SLE, comprising measuring Sema3A serum concentration in a subject in need thereof.

7 Claims, 7 Drawing Sheets
Specification includes a Sequence Listing.

(56) References Cited

OTHER PUBLICATIONS

Gronwall et al., (2012) IgM autoantibodies to distinct apoptosis-associated antigens correlate with protection from cardiovascular events and renal disease in patients with SLE. Clin Immunol 142(3): 390-398.
Gronwall et al., (2012) Protective Roles of Natural IgM Antibodies. Front Immunol 3: 66, pp. 1-10.
Guttmann-Raviv et al., (2007) Semaphorin-3A and semaphorin-3F work together to repel endothelial cells and to inhibit their survival by induction of apoptosis. J Biol Chem 282(36): 26294-26305.
Hayashi et al., (2012) Osteoprotection by semaphorin 3A. Nature 485(7396): 69-74.
Henno et al., (2009) Altered expression of angiogenesis and lymphangiogenesis markers in the uninvolved skin of plaque-type psoriasis. Br J Dermatol 160(3): 581-590.
Ji et al., (2009) Expression and function of semaphorin 3A and its receptors in human monocyte-derived macrophages. Hum Immunol 70(4): 211-217.
Kessel et al., (2012) Human CD19+CD25high B regulatory cells suppress proliferation of CD4+ T cells and enhance Foxp3 and CTLA-4 expression in T-regulatory cells. Autoimmun Rev 11(9): 670-677.
Kigel et al., (2008) Successful inhibition of tumor development by specific class-3 semaphorins is associated with expression of appropriate semaphorin receptors by tumor cells. PLoS One 3(9): e3287, 14 pages.
Kikutani et al., (2007) Immune semaphorins: increasing members and their diverse roles. Adv Immunol 93: 121-143.
Kolodkin et al., (1997) Neuropilin is a semaphorin III receptor. Cell 90(4): 753-762.
Kumanogoh et al., (2000) Identification of CD72 as a lymphocyte receptor for the class IV semaphorin CD100: a novel mechanism for regulating B cell signaling. Immunity 13(5): 621-631.
Kumanogoh et al., (2005) Requirement for CD100-CD72 interactions in fine-tuning of B-cell antigen receptor signaling and homeostatic maintenance of the B-cell compartment. Int Immunol 17(10): 1277-1282.
Kyttaris et al., (2005) Immune cells and cytokines in systemic lupus erythematosus: an update. Curr Opin Rheumatol 17(5): 518-522.
Lepelletier et al., (2006) Immunosuppressive role of semaphorin-3A on T cell proliferation is mediated by inhibition of actin cytoskeleton reorganization. Eur J Immunol 36(7): 1782-1793.
Lepelletier et al., (2007) Control of human thymocyte migration by Neuropilin-1/Semaphorin-3A-mediated interactions. Proc Natl Acad Sci U S A 104(13): 5545-5550.
Lepelletier et al., (2010) Galectin-1 and semaphorin-3A are two soluble factors conferring T-cell immunosuppression to bone marrow mesenchymal stem cell. Stem Cells Dev 19(7): 1075-1079.
Mizui et al., (2008) Neuropilin-1: the glue between regulatory T cells and dendritic cells? Immunity 28(3): 302-303.
Navarra et al., (2011) Efficacy and safety of belimumab in patients with active systemic lupus erythematosus: a randomised, placebo-controlled, phase 3 trial. Lancet 377(9767): 721-731.
Okuno et al., (2011) The role of immune semaphorins in multiple sclerosis. FEBS Lett 585(23): 3829-3835.
Perala et al., (2012) More than nervous: the emerging roles of plexins. Differentiation 83(1): 77-91.
Romaniec et al., (1987) Cloning and expression in *Escherichia coli* of Clostridium thermocellum DNA encoding β-glucosidase activity. Enzyme and Microbial Technology 9(8): 474-478.
Ruiz-Irastorza et al., (2010) Clinical efficacy and side effects of antimalarials in systemic lupus erythematosus: a systematic review. Ann Rheum Dis 69(1): 20-28.
Sarris et al., (2008) Neuropilin-1 expression on regulatory T cells enhances their interactions with dendritic cells during antigen recognition. Immunity 28(3): 402-413.
Sawaki et al., (2011) Intranasal administration of semaphorin-3A alleviates sneezing and nasal rubbing in a murine model of allergic rhinitis. J Pharmacol Sci 117(1): 34-44.
Shevach (2009) Mechanisms of foxp3+ T regulatory cell-mediated suppression. Immunity 30(5): 636-645.
Shi et al., (2000) The class IV semaphorin CD100 plays nonredundant roles in the immune system: defective B and T cell activation in CD100-deficient mice. Immunity 13(5): 633-642.
Solomon et al., (2011) Neuropilin-1 attenuates autoreactivity in experimental autoimmune encephalomyelitis. Proc Natl Acad Sci U S A 108(5): 2040-2045.
Summers et al., (2010) TLR9 and TLR4 are required for the development of autoimmunity and lupus nephritis in pristane nephropathy. J Autoimmun 35(4): 291-298.
Suzuki et al., (2008) Semaphorins and their receptors in immune cell interactions. Nat Immunol 9(1): 17-23.
Takamatsu et al., (2010) Regulation of immune cell responses by semaphorins and their receptors. Cell Mol Immunol 7(2): 83-88.
Tamagnone et al., (1999) Plexins are a large family of receptors for transmembrane, secreted, and GPI-anchored semaphorins in vertebrates. Cell 99(1): 71-80.
Tordjman et al., (2002) A neuronal receptor, neuropilin-1, is essential for the initiation of the primary immune response. Nat Immunol 3(5): 477-482.
Trivedi et al., (2009) Endosomal Toll-like receptors in autoimmunity: mechanisms for clinical diversity. Therapy 6(3): 433-442.
Tsubata (2012) Role of inhibitory BCR co-receptors in immunity. Infect Disord Drug Targets 12(3): 181-190.
Vadasz et al., (2012) Semaphorin 3A—a marker for disease activity and a potential putative disease-modifying treatment in systemic lupus erythematosus. Lupus 21(12): 1266-1270.
Vadasz et al., (2014) Semaphorins: their dual role in regulating immune-mediated diseases. Clin Rev Allergy Immunol 47(1): 17-25.
Vadasz et al., (2010) Neuropilins and semaphorins—from angiogenesis to autoimmunity. Autoimmun Rev 9(12): 825-829.
Vadasz et al., (2011) The involvement of immune semaphorins and neuropilin-1 in lupus nephritis. Lupus 20(14): 1466-1473.
Vadasz et al., (2011) The involvement of Neuropilin-1 and immune Semaphorin's in lupus nephritis. Ann Rheum Dis 70 (suppl 2): A47.
Vadasz et al., (2012) Semaphorin 3A is a marker for disease activity and a potential immunoregulator in systemic lupus erythematosus. Arthritis Res Ther 14(3): R146, 8 pages.
Wen et al., (2010) Plexin-A4-semaphorin 3A signaling is required for Toll-like receptor- and sepsis-induced cytokine storm. J Exp Med 207(13): 2943-2957.
Williams et al., (2007) Semaphorin 3A and 3F: key players in myelin repair in multiple sclerosis? Brain 130(Pt 10): 2554-2565.
Yazdani et al., (2006) The semaphorins. Genome Biol 7(3): 211, 14 pages.

\* cited by examiner

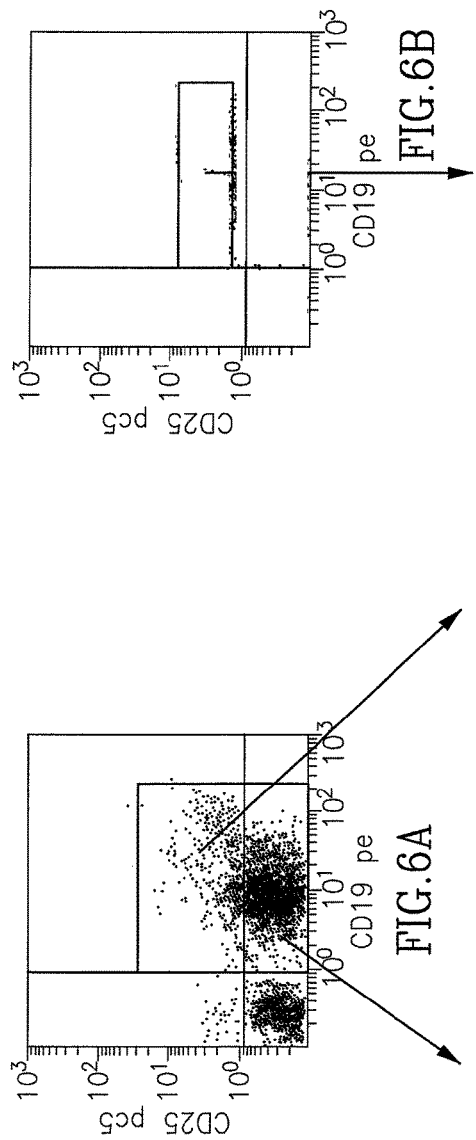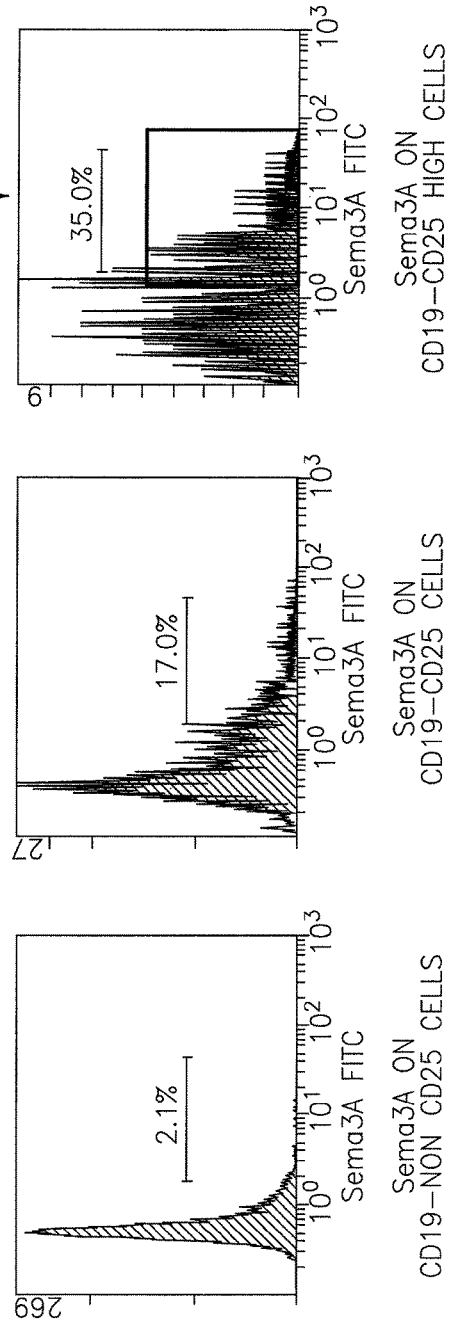

SEQUENCE LISTING

<160> NUMBER OF SEQ ID NOS: 3

<210> SEQ ID NO 1
<211> LENGTH: 771
<212> TYPE: PRT
<213> ORGANISM: Homo sapiens

<400> SEQUENCE: 1

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
            340                 345                 350

Leu Gly Pro Tyr Ala His Arg Asp Gly Pro Asn Tyr Gln Trp Val Pro
        355                 360                 365
```

```
Tyr Gln Gly Arg Val Pro Tyr Pro Arg Pro Gly Thr Cys Pro Ser Lys
    370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
                420                 425                 430

Gln Ile Val Val Asp Arg Val Asp Ala Glu Asp Gly Gln Tyr Asp Val
            435                 440                 445

Met Phe Ile Gly Thr Asp Val Gly Thr Val Leu Lys Val Val Ser Ile
450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
                500                 505                 510

Pro Leu His Arg Cys Asp Ile Tyr Gly Lys Ala Cys Ala Glu Cys Cys
            515                 520                 525

Leu Ala Arg Asp Pro Tyr Cys Ala Trp Asp Gly Ser Ala Cys Ser Arg
530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His His Asp Asn His His
                565                 570                 575

Gly His Ser Pro Glu Glu Arg Ile Ile Tyr Gly Val Glu Asn Ser Ser
            580                 585                 590

Thr Phe Leu Glu Cys Ser Pro Lys Ser Gln Arg Ala Leu Val Tyr Trp
            595                 600                 605

Gln Phe Gln Arg Arg Asn Glu Glu Arg Lys Glu Glu Ile Arg Val Asp
            610                 615                 620

Asp His Ile Ile Arg Thr Asp Gln Gly Leu Leu Leu Arg Ser Leu Gln
625                 630                 635                 640

Gln Lys Asp Ser Gly Asn Tyr Leu Cys His Ala Val Glu His Gly Phe
                645                 650                 655

Ile Gln Thr Leu Leu Lys Val Thr Leu Glu Val Ile Asp Thr Glu His
                660                 665                 670

Leu Glu Glu Leu Leu His Lys Asp Asp Gly Asp Gly Ser Lys Thr
                675                 680                 685

Lys Glu Met Ser Asn Ser Met Thr Pro Ser Gln Lys Val Trp Tyr Arg
            690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Gln Arg
                725                 730                 735

Pro Gly His Thr Pro Gly Asn Ser Asn Lys Trp Lys His Leu Gln Glu
                740                 745                 750

Asn Lys Lys Gly Arg Asn Arg Arg Thr His Glu Phe Glu Arg Ala Pro
            755                 760                 765

Arg Ser Val
    770
```

<210> SEQ ID NO 2
<211> LENGTH: 2316
<212> TYPE: DNA
<213> ORGANISM: Artificial Sequence
<220> FEATURE:
<223> OTHER INFORMATION: cDNA

<400> SEQUENCE: 2

| | | | | | |
|---|---|---|---|---|---|
| atgggctggt | taactaggat | tgtctgtctt | ttctggggag | tattacttac | agcaagagca | 60 |
| aactatcaga | tgggaagaa | caatgtgcca | aggctgaaat | tatcctacaa | agaaatgttg | 120 |
| gaatccaaca | atgtgatcac | tttcaatggc | ttggccaaca | gctccagtta | tcataccttc | 180 |
| cttttggatg | aggaacggag | taggctgtat | gttggagcaa | aggatcacat | attttcattc | 240 |
| gacctggtta | atatcaagga | ttttcaaaag | attgtgtggc | agtatctta | caccagaaga | 300 |
| gatgaatgca | agtgggctgg | aaaagacatc | ctgaaagaat | gtgctaattt | catcaaggta | 360 |
| cttaaggcat | ataatcagac | tcacttgtac | gcctgtggaa | cgggggcttt | tcatccaatt | 420 |
| tgcacctaca | ttgaaattgg | acatcatcct | gaggacaata | tttttaagct | ggagaactca | 480 |
| cattttgaaa | acggccgtgg | gaagagtcca | tatgacccta | agctgctgac | agcatccctt | 540 |
| ttaatagatg | gagaattata | ctctggaact | gcagctgatt | tatgggggcg | agactttgct | 600 |
| atcttccgaa | ctcttgggca | ccaccaccca | atcaggacag | agcagcatga | ttccaggtgg | 660 |
| ctcaatgatc | caaagttcat | tagtgcccac | ctcatctcag | agagtgacaa | tcctgaagat | 720 |
| gacaaagtat | acttttttctt | ccgtgaaaat | gcaatagatg | gagaacactc | tggaaaagct | 780 |
| actcacgcta | aataggtca | gatatgcaag | aatgactttg | gagggcacag | aagtctggtg | 840 |
| aataaatgga | caacattcct | caaagctcgt | ctgatttgct | cagtgccagg | tccaaatggc | 900 |
| attgacactc | attttgatga | actgcaggat | gtattcctaa | tgaactttaa | agatcctaaa | 960 |
| aatccagttg | tatatggagt | gtttacgact | tccagtaaca | ttttcaaggg | atcagccgtg | 1020 |
| tgtatgtata | gcatgagtga | tgtgagaagg | gtgttccttg | gtccatatgc | cacagggat | 1080 |
| ggacccaact | atcaatgggt | gccttatcaa | ggaagagtcc | cctatccacg | gccaggaact | 1140 |
| tgtcccagca | aaacatttgg | tggttttgac | tctacaaagg | accttcctga | tgatgttata | 1200 |
| acctttgcaa | gaagtcatcc | agccatgtac | aatccagtgt | ttcctatgaa | caatcgccca | 1260 |
| atagtgatca | aaacggatgt | aaattatcaa | tttacacaaa | ttgtcgtaga | ccgagtggat | 1320 |
| gcagaagatg | gacagtatga | tgttatgttt | atcggaacag | atgttgggac | cgttcttaaa | 1380 |
| gtagttttcaa | ttcctaagga | gacttggtat | gatttagaag | aggttctgct | ggaagaaatg | 1440 |
| acagttttc | gggaaccgac | tgctatttca | gcaatggagc | tttccactaa | gcagcaacaa | 1500 |
| ctatatattg | gttcaacggc | tggggttgcc | cagctcccctt | tacaccggtg | tgatatttac | 1560 |
| gggaaagcgt | gtgctgagtg | ttgcctcgcc | cgagacccct | actgtgcttg | ggatggttct | 1620 |
| gcatgttctc | gctatttttcc | cactgcaaag | agacgcacaa | gacgacaaga | tataagaaat | 1680 |
| ggagacccac | tgactcactg | ttcagactta | caccatgata | atcaccatgg | ccacagccct | 1740 |
| gaagagagaa | tcatctatgg | tgtagagaat | agtagcacat | ttttggaatg | cagtccgaag | 1800 |
| tcgcagagag | cgctggtcta | ttggcaattc | caggcgaa | atgaagagcg | aaaagaagag | 1860 |
| atcagagtgg | atgatcatat | catcaggaca | gatcaaggcc | ttctgctacg | tagtctacaa | 1920 |
| cagaaggatt | caggcaatta | cctctgccat | gcggtggaac | atgggttcat | acaaactctt | 1980 |
| cttaaggtaa | ccctggaagt | cattgacaca | gagcatttgg | aagaacttct | tcataaagat | 2040 |
| gatgatggag | atggctctaa | gaccaaagaa | atgtccaata | gcatgacacc | tagccagaag | 2100 |

```
gtctggtaca gagacttcat gcagctcatc aaccaccca atctcaacac aatggatgag   2160
ttctgtgaac aagtttggaa aagggaccga aaacaacgtc ggcaaaggcc aggacatacc   2220
ccagggaaca gtaacaaatg gaagcactta caagaaaata agaaggtag aaacaggagg    2280 acccacgaat tgagagggc acccaggagt gtctga                              2316
```

<210> SEQ ID NO 3
<211> LENGTH: 779
<212> TYPE: PRT
<213> ORGANISM: Artificial Sequence
<220> FEATURE:
<223> OTHER INFORMATION: Recombinant polypeptide

<400> SEQUENCE: 3

```
Met Gly Trp Leu Thr Arg Ile Val Cys Leu Phe Trp Gly Val Leu Leu
1               5                   10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
    210                 215                 220

Lys Phe Ile Ser Ala His Leu Ile Ser Glu Ser Asp Asn Pro Glu Asp
225                 230                 235                 240

Asp Lys Val Tyr Phe Phe Phe Arg Glu Asn Ala Ile Asp Gly Glu His
                245                 250                 255

Ser Gly Lys Ala Thr His Ala Arg Ile Gly Gln Ile Cys Lys Asn Asp
            260                 265                 270

Phe Gly Gly His Arg Ser Leu Val Asn Lys Trp Thr Thr Phe Leu Lys
        275                 280                 285

Ala Arg Leu Ile Cys Ser Val Pro Gly Pro Asn Gly Ile Asp Thr His
    290                 295                 300

Phe Asp Glu Leu Gln Asp Val Phe Leu Met Asn Phe Lys Asp Pro Lys
305                 310                 315                 320
```

-continued

```
Asn Pro Val Val Tyr Gly Val Phe Thr Thr Ser Ser Asn Ile Phe Lys
                325                 330                 335
Gly Ser Ala Val Cys Met Tyr Ser Met Ser Asp Val Arg Arg Val Phe
            340                 345                 350
Leu Gly Pro Tyr Ala His Arg Asp Gly Pro Asn Tyr Gln Trp Val Pro
        355                 360                 365
Tyr Gln Gly Arg Val Pro Tyr Pro Arg Pro Gly Thr Cys Pro Ser Lys
    370                 375                 380
Thr Phe Gly Gly Phe Asp Ser Thr Lys Asp Leu Pro Asp Asp Val Ile
385                 390                 395                 400
Thr Phe Ala Arg Ser His Pro Ala Met Tyr Asn Pro Val Phe Pro Met
            405                 410                 415
Asn Asn Arg Pro Ile Val Ile Lys Thr Asp Val Asn Tyr Gln Phe Thr
        420                 425                 430
Gln Ile Val Val Asp Arg Val Asp Ala Glu Asp Gly Gln Tyr Asp Val
    435                 440                 445
Met Phe Ile Gly Thr Asp Val Gly Thr Val Leu Lys Val Val Ser Ile
450                 455                 460
Pro Lys Glu Thr Trp Tyr Asp Leu Glu Glu Val Leu Leu Glu Glu Met
465                 470                 475                 480
Thr Val Phe Arg Glu Pro Thr Ala Ile Ser Ala Met Glu Leu Ser Thr
            485                 490                 495
Lys Gln Gln Gln Leu Tyr Ile Gly Ser Thr Ala Gly Val Ala Gln Leu
        500                 505                 510
Pro Leu His Arg Cys Asp Ile Tyr Gly Lys Ala Cys Ala Glu Cys Cys
    515                 520                 525
Leu Ala Arg Asp Pro Tyr Cys Ala Trp Asp Gly Ser Ala Cys Ser Arg
            530                 535                 540
Tyr Phe Pro Thr Ala Lys Arg Arg Thr Arg Arg Gln Asp Ile Arg Asn
545                 550                 555                 560
Gly Asp Pro Leu Thr His Cys Ser Asp Leu His His Asp Asn His His
            565                 570                 575
Gly His Ser Pro Glu Glu Arg Ile Ile Tyr Gly Val Glu Asn Ser Ser
        580                 585                 590
Thr Phe Leu Glu Cys Ser Pro Lys Ser Gln Arg Ala Leu Val Tyr Trp
    595                 600                 605
Gln Phe Gln Arg Arg Asn Glu Glu Arg Lys Glu Ile Arg Val Asp
        610                 615                 620
Asp His Ile Ile Arg Thr Asp Gln Gly Leu Leu Leu Arg Ser Leu Gln
625                 630                 635                 640
Gln Lys Asp Ser Gly Asn Tyr Leu Cys His Ala Val Glu His Gly Phe
            645                 650                 655
Ile Gln Thr Leu Leu Lys Val Thr Leu Glu Val Ile Asp Thr Glu His
        660                 665                 670
Leu Glu Glu Leu Leu His Lys Asp Asp Gly Asp Gly Ser Lys Thr
    675                 680                 685
Lys Glu Met Ser Asn Ser Met Thr Pro Ser Gln Lys Val Trp Tyr Arg
690                 695                 700
Asp Phe Met Gln Leu Ile Asn His Pro Asn Leu Asn Thr Met Asp Glu
705                 710                 715                 720
Phe Cys Glu Gln Val Trp Lys Arg Asp Arg Lys Gln Arg Gln Arg
            725                 730                 735
```

```
Pro Gly His Thr Pro Gly Asn Ser Asn Lys Trp Lys His Leu Gln Glu
            740             745             750

Asn Lys Lys Gly Arg Asn Arg Arg Thr His Glu Phe Glu Arg Ala Pro
        755             760             765

Arg Ser Val Asp Tyr Lys Asp Asp Asp Lys
    770             775
```

SEMAPHORIN 3A FOR TREATMENT OF SYSTEMIC LUPUS ERYTHEMATOSUS

The Sequence Listing submitted in text format (.txt) filed on Dec. 9, 2015, named "SequenceListing.txt", created on Dec. 7, 2015, 16.2 KB), is incorporated herein by reference.

FIELD OF THE INVENTION

The present invention relates to Semaphorin 3A (Sema3A) and its use in treatment and prognosis of Systemic Lupus Erythematosus (SLE). The present invention provides methods of treating a subject afflicted with SLE, comprising administering to the subject a pharmaceutical composition comprising Sema3A, and methods for prognosis of SLE, comprising measuring Sema3A serum concentration in a subject in need thereof.

BACKGROUND OF THE INVENTION

Systemic Lupus Erythematosus (SLE)

Autoimmune diseases arise following an autoimmune response of the body against substances and tissues normally present in the body, resulting in continuous production of autoantibodies. Autoantibodies are able to activate the complement system and are deposited in many sites, thus inducing multi-organ inflammatory reactions and possibly damage to organs such as the kidneys. More than 5% of the world's population suffers from at least one of many autoimmune diseases, such as lupus, rheumatoid arthritis, scleroderma and others.

Systemic Lupus Erythematosus (SLE) is an autoimmune disease manifested as a chronic syndrome with a multifactorial etiology and multiple symptoms affecting many organs such as the skin, the kidneys and the brain. The multifactorial complexity of SLE includes an overproduction of B cell activating factor (BAFF), an escape of auto-reactive B cells from apoptosis and a dis-balanced production of various inflammatory and protective cytokines Severe SLE involves glomerulonephritis, complications in the central nervous system, and recurrent thrombosis.

Several symptoms that are associated with SLE include: an increase in anti-cardiolipin auto-antibodies directed against cardiolipin present in the mitochondrial inner-membrane, an increase in anti-double-stranded DNA (anti-ds-DNA) antibodies, a decrease in complement-system component concentration and Lupus Nephritis (LN)—an inflammation of the kidney leading to defects in renal function and possibly renal failure. Lupus Nephritis is often characterized by glomerulonephritis—an inflammation of the kidney glomeruli.

The disease course of SLE is unpredictable, comprising periods of illness (called flares) alternating with remissions and displaying symptoms that vary widely. In order to evaluate SLE disease activity, a scoring index is commonly used. The Systemic Lupus Erythematosus Disease Activity Index (SLEDAI) is the most commonly used scoring system to evaluate SLE disease activity (Bombardier C. et al., 1992, Arthritis and Rheumatism, 35(6):630-640). In order to arrive at a SLEDAI score, each patient is examined for the presence of 24 clinical characteristics in the last 10 days. Each clinical characteristic is assigned a value and the sum of these values is the patient's SLEDAI score.

There is no cure for SLE, thus treatment is focused on reducing the severity of symptoms and/or on prevention of symptoms. For many years, standard therapy for SLE included anti-malarials, steroids and immunosuppressive drugs. Though efficient in improving quality of life, survival and well-being, these treatments still induce many undesired side effects.

Publication EP2123280 discloses an agent for prevention and/or treatment of systemic lupus erythematosus, which comprises, in combination, 2-benzyl-5-(4-chlorophenyl)-6-[4-(methylthio)phenyl]-2H-pyrida zine-3-one or a solvate thereof and a corticosteroid.

Publication WO2004/093647 discloses a method for identifying or monitoring SLE in an individual, including quantitating complement component C4d on the surfaces of platelets and comparing the amounts of C4d to reference levels of C4d on platelets of individuals without SLE and/or on platelets of the individual obtained at a different time.

Semaphorins and Semaphorin 3A

Semaphorins are a family of membrane bound and soluble proteins classified into eight sub-classes based on their structural domains. Semaphorins mainly regulate focal adhesion assembly/disassembly and induce cytoskeletal remodeling, thus affecting cell shape, cell attachment to the extracellular matrix, cell motility, and cell migration. Although Semaphorins were originally identified as affecting axon guidance during development of the nervous system, they are now thought to fulfill diverse physiological roles including organogenesis, vascularization, angiogenesis, neuronal apoptosis, and neoplastic transformation. Additionally, recent studies pointed to the involvement of Neuropilin-1 and certain Semaphorins in the regulation of the immune system, and thus these Semaphorins are denoted "immune Semaphorins" (Kikutani H. et al., 2007, Advances in Immunology, 93:121-143).

The seven class-3 Semaphorins (Sema3s), designated by the letters A-G, are the only vertebrate secreted Semaphorins. Neuropilins (Nrps) and the type A/D family Plexins (Plexin-A1, -A2, and -A3, and Plexin-D1) act as receptors for Sema3s. Each Sema3 family member shows distinct binding preference for Nrps. Each Sema3-Nrp complex associates with specific plexins to mediate downstream signaling. Most membrane-bound vertebrate Semaphorins directly bind plexins, while class-3 Semaphorins require Neuropilins as obligate co-receptors.

Semaphorin 3A (Sema3A), a class-3 secreted member of the Semaphorin family, has been established as an axonal guidance factor during development. Interestingly, several lines of evidence suggest that Sema3A also affects immune cell functions. Sema3A has been shown to be expressed by activated T cells and inhibit T cell proliferation and cytokine secretion (Catalano, A et al, 2006, Blood 107: 3321-3329; Lepelletier, Y. et al., 2006, Eur. J. Immunol. 36: 1782-1793). Moreover, the expression of Sema3A, Neuropilin 1 (NP-1), Neuropilin 2 (NP-2), and Plexins was found to be increased on differentiating macrophages and on activated T cells (Ji J D et al., 2009, Human Immunol., 70(4): 211-7). Additionally, Neuropilin-1 expression on regulatory T cells has been shown to enhance interactions with immature dendritic cells (DCs) during antigen recognition, resulting in higher sensitivity to limiting amounts of antigen (Sarris, M. et al., 2008, Immunity, 28: 402-13).

A recent study has shown that overexpression of Sema3A in a mouse model of collagen-induced arthritis resulted in reduced incidence, disease severity, and articular inflammation. Moreover, in line with results in arthritic mice, the study showed a defective Sema3A expression in $CD4^+$ T cells derived from patients with rheumatoid arthritis (Catalano A. et al., 2010, J. Immunol., 185: 6373-83).

In another study, kidney biopsies from lupus glomerulonephritis (LGN) patients showed stronger staining with anti-NP-1, anti-Semaphorin 3A and anti-Semaphorin 4A antibodies as compared with either normal biopsies or biopsies from patients with primary nephropathy and proteinuria (Vadasz Z. et al., 2011, Lupus, 20:1466-1473). A subsequent study has shown that Sema 3A serum levels in SLE patients are significantly lower than in healthy individuals (Vadasz Z. et al, 2012, Arthritis Research & Therapy, 14:R146).

U.S. Application Publication No. 2012/0251539 discloses a method of treating an immune-related disorder in a subject, comprising administering to the subject an effective amount of a Sema3A inhibitor, resulting in reduced Sema3A activity in the subject.

There is still an unmet need, however, for a safe and effective treatment for Systemic Lupus Erythematosus.

SUMMARY OF THE INVENTION

The present invention provides methods of treatment for Systemic Lupus Erythematosus (SLE), comprising administration of a pharmaceutical composition comprising isolated Semaphorin 3A to a subject in need thereof. The present invention further provides methods for determining the efficiency of a treatment for Systemic Lupus Erythematosus and methods for prognosis of change in Systemic Lupus Erythematosus disease activity.

The present invention is based in part on the unexpected discovery that serum concentration of Semaphorin 3A is inversely correlated to Systemic Lupus Erythematosus disease activity. The present invention if further based on the unexpected discovery that incubation of B cells derived from SLE patients with Semaphorin 3A containing media resulted in a decrease in Toll-Like Receptor 9 (TLR-9) expression on the cells, as exemplified herein below. As known in the art, TLR-9 expression on B-cells is associated with production of IL-10 and IL-6 cytokines and production of anti-dsDNA antibodies in SLE patients.

According to one aspect, the present invention provides a method for treating Systemic Lupus Erythematosus, the method comprising administering to a subject in need thereof a pharmaceutical composition comprising a therapeutically effective amount of isolated Semaphorin 3A.

According to some embodiments, Semaphorin 3A has a sequence having at least 90% homology to human Semaphorin 3A as set forth by SEQ ID NO: 1. According to some embodiments, Semaphorin 3A has a sequence as set forth by SEQ ID NO: 1. According to some embodiments, a subject in need thereof is a subject afflicted by Systemic Lupus Erythematosus.

According to some embodiments, treating a subject using a pharmaceutical composition comprising Semaphorin 3A results in at least one clinical outcome selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, treating a subject using a pharmaceutical composition comprising isolated Semaphorin 3A results in a decrease in the Systemic Lupus Erythematosus Disease Activity Index (SLEDAI) value of the subject.

According to some embodiments, administering to a subject in need thereof is by a route selected from the group consisting of: intravenous, intraarterial, subcutaneous and via direct injection into a tissue or an organ. Each possibility represents a separate embodiment of the present invention.

According to some embodiments, treating a subject using a pharmaceutical composition comprising isolated Semaphorin 3A further comprises administering an additional Systemic Lupus Erythematosus treatment to the subject. According to some embodiments, the Systemic Lupus Erythematosus treatment is selected from the group consisting of: a corticosteroid, a cytotoxic drug, a non-steroidal anti-inflammatory drug, an anti-malarial drug, a disease-modifying anti-rheumatic drug, an immunosuppressive drug, an analgesic, intravenous immunoglobulins and a combination thereof. Each possibility represents a separate embodiment of the present invention.

According to another aspect, the present invention provides a method for determining efficacy of a treatment for Systemic Lupus Erythematosus in a subject in need thereof, the method comprising: making a first measurement of serum Semaphorin 3A concentration in a subject in need thereof prior to administration of a treatment for Systemic Lupus Erythematosus to the subject; making a second measurement of serum Semaphorin 3A concentration in the subject following the treatment; and comparing the first measurement and the second measurement, wherein an increase in serum Semaphorin 3A concentration from the first to the second measurement is indicative of the treatment being efficacious.

According to another aspect, the present invention provides a method for prognosis of change in Systemic Lupus Erythematosus disease activity in a subject in need thereof, the method comprising: making a first measurement of serum Semaphorin 3A concentration in a subject in need thereof; making a second measurement of serum Semaphorin 3A concentration in the subject at a later time point than said first measurement; and comparing said first measurement and said second measurement; wherein an increase in serum Semaphorin 3A concentration from the first to the second measurement is indicative of a decrease in disease activity; and wherein a decrease in serum Semaphorin 3A concentration from the first to the second measurement is indicative of an increase in disease activity.

According to some embodiments, the efficacy of a treatment for Systemic Lupus Erythematosus is indicated by at least one clinical outcome selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, the efficacy of a treatment for Systemic Lupus Erythematosus is indicated by a decrease in the Systemic Lupus Erythematosus Disease Activity Index (SLEDAI) value of the treated subject. According to some embodiments, the increase in serum Semaphorin 3A concentration following an efficacious treatment for SLE is an increase of at least 10%. According to some embodiments, the increase in serum Semaphorin 3A concentration following an efficacious treatment for SLE is an increase to a level of at least 50 ng/ml.

According to some embodiments, a decrease in SLE disease activity is characterized by at least one clinical effect selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, a decrease in SLE disease activity is evidenced by a decrease in the value of the Systemic Lupus Erythematosus Disease Activity Index of the subject.

According to some embodiments, an increase in SLE disease activity is characterized by at least one clinical effect selected from the group consisting of: deterioration in renal function, an increase in anti-dsDNA antibody concentration in the serum, an increase in anti-Cardiolipin antibody concentration in the serum, a decrease in serum concentration of complement factor C3 and a decrease in serum concentration of complement factor C4. Each possibility represents a separate embodiment of the present invention. According to some embodiments, an increase in SLE disease activity is evidenced by an increase in the value of the Systemic Lupus Erythematosus Disease Activity Index of the subject.

According to some embodiments, serum Semaphorin 3A concentration measurement of up to 50 ng/ml is indicative of Lupus Nephritis.

Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 6(A-E) show flow cytometry scatter micrographs plotting CD19 positive B-cells vs. CD25 positive B-Cells (A,B) and micrographs representing Sema3A expression on (C) $CD19^-CD25^{low}$ B-cells, (D) $CD19^+CD25^{low}$ B cells and (E) $CD19^+CD25^{high}$ B cells.

DETAILED DESCRIPTION OF THE INVENTION

Figure 1:
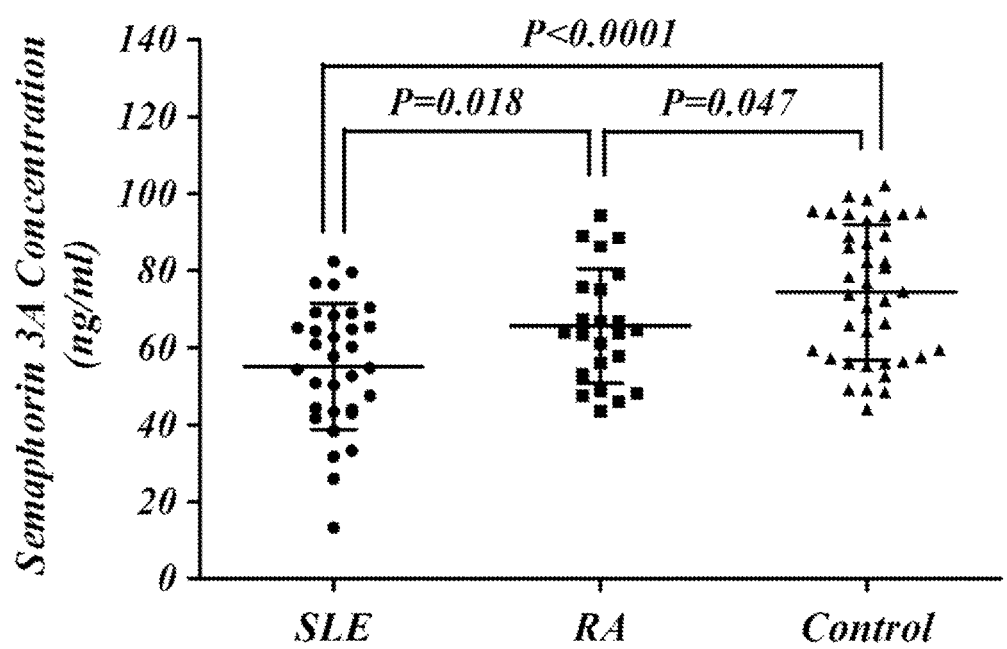
FIG. 1 is a dot plot comparing Sema3A serum concentration in Systemic Lupus Erythematosus patients (SLE), Rheumatoid Arthritis patients (RA), as a disease control group, and healthy subjects (Control).

The present invention provides, according to one aspect, a method for treating Systemic Lupus Erythematosus (SLE), the method comprising administering to a subject in need thereof a pharmaceutical composition comprising a therapeutically effective amount of isolated Semaphorin 3A.

According to some embodiments, the present invention provides a pharmaceutical composition comprising isolated Semaphorin 3A for use in treating Systemic Lupus Erythematosus (SLE). According to some embodiments, the present invention provides a pharmaceutical composition comprising isolated Semaphorin 3A for use in treating a subject afflicted with Systemic Lupus Erythematosus (SLE).

As used herein, the terms "Systemic Lupus Erythematosus" and "SLE" are used interchangeably. According to some embodiments, treating SLE refers to ameliorating and/or preventing at least one clinical symptom of SLE. Each possibility represents a separate embodiment of the present invention. According to some embodiments, treating SLE refers to ameliorating preventing at least one clinical symptom of SLE. According to other embodiments, treating SLE refers to ameliorating and/or preventing symptoms other than symptoms of Lupus Nephritis. Each possibility represents a separate embodiment of the present invention. As used herein, the term "symptom" and "clinical symptom" are used interchangeably.

According to some embodiments, treating SLE refers to inducing a decrease in disease activity. According to some embodiments, treating SLE refers to inducing a decrease in disease activity as evidenced by a decrease in Systemic Lupus Erythematosus Disease Activity Index (SLEDAI) value in the treated subject. It is to be noted that a lower SLEDAI value is indicative of lower SLE disease activity.

According to some embodiments, treating SLE refers to shortening a flare period present at the time of treatment. According to some embodiments, treating SLE refers to shortening flare periods. As used herein, the term "flare period" refers to a time period in which at least one SLE symptom is manifested. According to some embodiments, treating SLE refers to increasing serum concentration of Semaphorin 3A. According to some embodiments, treating SLE refers to increasing Semaphorin 3A serum concentration to about 50 ng/ml or higher. Each possibility represents a separate embodiment of the present invention. As used hererin, the term "about" refers to +/−10%, preferably +/−5%, most preferably +/−1%. Each possibility represents a separate embodiment of the present invention. According to some embodiments, treating SLE refers to increasing serum concentration of Semaphorin 3A to at least 50 ng/ml in a subject in need thereof. According to some embodiments, treating SLE refers to increasing serum concentration of Semaphorin 3A by at least 10%, preferably by at least 20%. Each possibility represents a separate embodiment of the present invention. Without wishing to be bound by theory or mechanism, the increase in Semaphorin 3A serum concentration following treating according to the present invention is dependent on the specific physiological parameters of each subject. Therefore, an increase in Semaphorin 3A of less than 10% may be accounted as treating according to certain embodiments.

According to some embodiments, a subject in need thereof is a subject afflicted with SLE. According to other embodiments, a subject in need thereof is other than a subject afflicted with Lupus Nephritis.

Symptoms of SLE may include, but are not limited to, symptoms selected from the group consisting of: systemic symptoms, skin and mucosal symptoms, muscular and articular symptoms, renal symptoms, neurological and/or neuropsychiatric symptoms, cardiovascular symptoms, pulmonary symptoms, gastrointestinal symptoms, hematopoietic symptoms and a combination thereof. Each possibility represents a separate embodiment of the present invention.

According to some embodiments, treating SLE refers to ameliorating and/or preventing at least one symptom caused by SLE selected from the group consisting of: systemic symptoms, skin and mucosal symptoms, muscular and articular symptoms, renal symptoms, neurological and/or neuropsychiatric symptoms, cardiovascular symptoms, pulmonary symptoms, gastrointestinal symptoms, hematopoietic symptoms and a combination thereof. Each possibility represents a separate embodiment of the present invention.

According to some embodiments, systemic symptoms comprise symptoms selected from the group consisting of: systemic malaise, fatigue, fever and a combination thereof. Each possibility represents a separate embodiment of the present invention.

According to some embodiments, skin and mucosal symptoms comprise symptoms selected from the group consisting of: malar rash (butterfly erythema), discoid rash, chilblains, alopecia, mouth ulcers and a combination thereof. Each possibility represents a separate embodiment of the present invention.

According to some embodiments, muscular and articular symptoms comprise symptoms selected from the group consisting of: muscular pain, articular pain, arthritis and a combination thereof. Each possibility represents a separate embodiment of the present invention.

According to some embodiments, renal symptoms comprise symptoms selected from the group consisting of: glomerulonephritis, proteinuria, hematuria, renal failure, end-stage renal failure and a combination thereof. Each possibility represents a separate embodiment of the present invention.

As used herein, the terms "Lupus Nephritis" and "LN" are used interchangeably and refer to SLE in which renal inflammation is manifested. According to some embodiments, Lupus Nephritis refers to SLE in which glomerulonephritis is manifested. As used herein, the term "glomerulonephritis" refers to inflammation of glomeruli in the kidney. According to some embodiments, SLE patients with Lupus Nephritis develop renal failure. According to some embodiments, Lupus Nephritis patients manifest at least one symptom selected from the group consisting of: glomerulonephritis, proteinuria, hematuria, elevated blood pressure, renal failure, end-stage renal failure and a combination thereof. Each possibility represents a separate embodiment of the present invention. According to some embodiments, treating Lupus Nephritis results in amelioration and/or prevention of at least one symptom selected from the group consisting of: glomerulonephritis, proteinuria, hematuria, renal failure, end-stage renal failure and a combination thereof. Each possibility represents a separate embodiment of the present invention.

As used herein, the terms "patient" and "subject" are used interchangeably.

According to some embodiments, neurological and/or neuropsychiatric symptoms comprise symptoms selected from the group consisting of: headaches, cognitive dysfunction, mood disorder, cerebrovascular disease, seizures, polyneuropathy, anxiety disorder, psychosis, intracranial hypertension syndrome, acute confusional state, Guillain-Barré syndrome, aseptic meningitis, autonomic disorder, demyelinating syndrome, mononeuropathy, movement disorder, myasthenia gravis-like symptoms, myelopathy, cranial neuropathy, plexopathy, blood-brain barrier damage, depression and a combination thereof. Each possibility represents a separate embodiment of the present invention.

According to some embodiments, cardiovascular symptoms comprise symptoms selected from the group consisting of: pericarditis, myocarditis, endocarditis, atherosclerosis, tachycardia, arrhythmia, aortic valve insufficiency, mitral valve insufficiency, thrombophlebitis and a combination thereof. Each possibility represents a separate embodiment of the present invention.

According to some embodiments, pulmonary symptoms comprise symptoms selected from the group consisting of: pleuritis, pleural effusion, lupus pneumonitis, chronic diffuse interstitial lung disease, pulmonary hypertension, pulmonary emboli, pulmonary hemorrhage, shrinking lung syndrome and a combination thereof. Each possibility represents a separate embodiment of the present invention.

According to some embodiments, gastrointestinal symptoms comprise symptoms selected from the group consisting of: mesenteric vasculitis, lupus peritonitis, abdominal pain and a combination thereof. Each possibility represents a separate embodiment of the present invention.

According to some embodiments, hematopoietic symptoms comprise symptoms selected from the group consisting of: anemia, low platelet and/or white blood cell count, anti-phospholipid antibody syndrome, presence of anti-cardiolipin antibodies, presence of lupus-anticoagulant, presence of anti-dsDNA antibodies and a combination thereof. Each possibility represents a separate embodiment of the present invention.

According to some embodiments, symptoms of SLE include reduced expression of Semaphorin 3A on $CD19^+CD25^{high}$ B cells, reduced expression of Neuropilin-1 on $CD19^+CD25^{high}$ B cells and a combination thereof. Each possibility represents a separate embodiment of the present invention. According to some embodiments, healthy subjects and SLE patients show substantially similar expression level of Semaphorin 3A on T cells.

According to some embodiments, treating of SLE using the composition of the invention results in at least one clinical outcome selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. Without wishing to be bound by any theory or mechanism, administration of the composition of the invention to a subject afflicted with SLE may result in a decrease in expression of Toll-Like Receptor 9 and/or inflammatory cytokines, such as, but not limited to, IL-1, IL-6, IL-17 and interferon-gamma, in $CD19^+/CD27^+$ B cells of the subject. According to some embodiments, the present invention provides a method for decreasing Toll-Like Receptor 9 expression on $CD19^+/CD27^+$ B cells of a subject afflicted with SLE, the method comprising administration of a composition comprising therapeutically effective amount of isolated Semaphorin 3A.

According to some embodiments, a therapeutically effective amount refers to an amount sufficient to induce a decrease in SLE disease activity. According to some embodiments, a therapeutically effective amount refers to an amount sufficient to increase Semaphorin 3A serum concentration by at least 10% in a subject in need thereof. According to some embodiments, a therapeutically effective amount refers to an amount sufficient to increase Semaphorin 3A serum concentration to at least 50 ng/ml in a subject in need thereof. According to some embodiments, a therapeutically effective amount refers to an amount sufficient to ameliorate and/or prevent at least one clinical symptom of SLE. Each possibility represents a separate embodiment of the present invention.

As used herein, the term "pharmaceutical composition", "composition", "the composition of the invention" and "the composition" are used interchangeably and refer to a composition comprising isolated Semaphorin 3A. According to some embodiments, Semaphorin3A is mammalian Semaphorin 3A. According to some embodiments, Semaphorin3A is human Semaphorin 3A. According to some embodiments, Semaphorin 3A is recombinant Semaphorin3A.

According to some embodiments, Semaphorin 3A refers to a polypeptide having at least 90% homology to Semaphorin 3A. According to some embodiments, Semaphorin 3A has a sequence having at least 90% homology to human Semaphorin 3A as set forth by SEQ ID NO: 1. According to some embodiments, a polypeptide having at least 90% homology to Semaphorin3A is about as functional as Semaphorin3A. According to preferred embodiments, Semaphorin 3A as used herein is human Semaphorin 3A having an amino-acid sequence as set forth in SEQ ID NO: 1. The polynucleotide sequence as set forth in SEQ ID NO: 2 corresponds to the cDNA encoding human Semaphorin 3A as set forth in SEQ ID NO: 1.

According to some embodiments, Semaphorin 3A according to the present invention further comprises a protein tag. According to some embodiments, Semaphorin3A comprises a protein tag upon production but the tag is cleaved and/or removed from Semaphorin3A prior to incorporation into the composition of the invention. Each possibility represents a separate embodiment of the present invention. Cleavage and/or removal of a tag may be performed by any methods known in the art, such as, but not limited to, enzymatic and/or chemical cleaving, so as long as Semaphorin 3A remains functional. According to some embodiments, functional Semaphorin3A refers to Semaphorin 3A which is able to reduce SLE disease activity and/or ameliorate at least one SLE symptom. Each possibility represents a separate embodiment of the present invention.

As used herein, the term "protein tag" refers to a peptide sequence bound to the N-terminus or C-terminus of a protein. According to some embodiments, protein tags may comprise glycoproteins. According to some embodiments, protein tags may be used for separation and/or purification of the bound proteins. Each possibility represents a separate embodiment of the present invention. Non-limiting examples of protein tags are: Myc, Human influenza hemaglutinin (HA), Flag, His, Gluthathione-S-Transferase (GST) and a combination thereof. Each possibility represents a separate embodiment of the present invention.

As used herein, the term "isolated" means either: 1) separated from at least some of the components with which it is usually associated in nature; 2) prepared or purified by a process that involves the hand of man; and/or 3) not occurring in nature.

According to some embodiments, isolated Semaphorin 3A as disclosed herein may be produced by recombinant or chemical synthetic methods. According to some embodiments, Semaphorin 3A as disclosed herein may be produced by recombinant methods from genetically-modified host cells. Any host cell known in the art for the production of recombinant proteins may be used for the present invention. In some embodiments, the host cell is a prokaryotic cell. Representative, non-limiting examples of appropriate prokaryotic hosts include bacterial cells, such as cells of *Escherictahia coli* and *Bacillus subtilis*. In other embodiments, the host cell is a eukaryotic cell. In some exemplary embodiments, the host cell is a fungal cell, such as yeast. Representative, non-limiting examples of appropriate yeast cells include *Saccharomyces cerevisiae* and *Pichia pastoris*. In additional exemplary embodiments, the host cell is a plant cell.

Following are non-limiting examples of recombinant and chemical synthetic methods suitable for production of Semaphorin 3A, according to the present invention.

Recombinant Expression

As used herein, the term "gene" has its meaning as understood in the art. In general, a gene is taken to include gene regulatory sequences (e.g. promoters, enhancers, etc.) and/or intron sequences, in addition to coding sequences (open reading frames).

As used herein, the terms "polypeptide" and "protein" are used interchangeably and refer to a polymer of amino acid residues.

As used herein, the term "DNA construct" refers to an artificially assembled or isolated nucleic acid molecule which comprises a gene of interest or a coding region of interest. According to some embodiments, a gene of interest is a gene encoding human Semaphorin 3A. According to some embodiments, a coding region of interest is a coding region encoding Semaphorin 3A. According to some embodiments, a coding region of interest is a coding region encoding for human Semaphorin 3A as set forth in SEQ ID NO:2.

As used herein, the term "vector" refers to any recombinant polynucleotide construct (such as a DNA construct) that may be used for the purpose of transformation, i.e. the introduction of heterologous DNA into a host cell. One exemplary type of vector is a "plasmid" which refers to a circular double stranded DNA loop into which additional DNA segments can be ligated. Another exemplary type of vector is a viral vector, wherein additional DNA segments can be ligated into the viral genome. Certain vectors are capable of autonomous replication in a host cell into which they are introduced.

As used herein, a "primer" defines an oligonucleotide which is capable of annealing to (hybridizing with) a target nucleotide sequence, thereby creating a double stranded region which can serve as an initiation point for DNA synthesis under suitable conditions.

As used herein, the terms "transformation" refers to the introduction of foreign DNA into cells. The terms "transformants" or "transformed cells" include the primary transformed cell and cultures derived from that cell regardless to the number of transfers. All progeny may not be precisely identical in DNA content, due to deliberate or inadvertent mutations. Mutant progeny that have the same functionality as screened for in the originally transformed cell are included in the definition of transformants.

Semaphorin 3A may be synthesized by expressing a polynucleotide molecule encoding Semaphorin 3A in a host cell, for example, a microorganism cell transformed with the nucleic acid molecule.

DNA sequences encoding wild type polypeptides, such as Semaphorin 3A, may be isolated from any cell producing them, using various methods well known in the art (see for example, Sambrook, et al., Molecular Cloning: A Laboratory Manual, Third Edition, Cold Spring Harbor, N.Y., (2001)). For example, a DNA encoding the wild-type polypeptide may be amplified from genomic DNA by polymerase chain reaction (PCR) using specific primers, constructed on the basis of the nucleotide sequence of the known wild type sequence. Suitable techniques are well known in the art, described for example in U.S. Pat. Nos. 4,683,195; 4,683,202; 4,800,159 and 4,965,188.

The genomic DNA may be extracted from the cell prior to the amplification using various methods known in the art, see for example, Marek P. M et al., "Cloning and expression in *Escherichia coli* of *Clostridium thermocellum* DNA encoding p-glucosidase activity", Enzyme and Microbial Technology Volume 9, Issue 8, August 1987, Pages 474-478.

The isolated polynucleotide encoding the wild type polypeptide may be cloned into a vector, such as, but not limited to, the pET28a plasmid.

Upon isolation and cloning of the polynucleotide encoding the wild type polypeptide, desired mutation(s) may be introduced by modification at one or more base pairs, using methods known in the art, such as for example, site-specific mutagenesis, cassette mutagenesis, recursive ensemble mutagenesis and gene site saturation mutagenesis. Methods are also well known for introducing multiple mutations into a polynucleotide. For example, introduction of two and/or three mutations can be performed using commercially available kits, such as the QuickChange site-directed mutagenesis kit (Stratagene).

An alternative method to producing a polynucleotide with a desired sequence is the use of a synthetic gene. A polynucleotide encoding a desired polypeptide may be prepared synthetically, for example using the phosphoroamidite method (see, Beaucage et al., Curr Protoc Nucleic Acid Chem. 2001 May; Chapter 3:Unit 3.3; Caruthers et al., Methods Enzymol. 1987, 154:287-313).

The polynucleotide thus produced may then be subjected to further manipulations, including one or more of purification, annealing, ligation, amplification, digestion by restriction endonucleases and cloning into appropriate vectors. The polynucleotide may be ligated either initially into a cloning vector, or directly into an expression vector that is appropriate for its expression in a particular host cell type.

In the case of a fusion protein, or a protein fused with a protein tag, different polynucleotides may be ligated to form one polynucleotide. For example, different polynucleotides may be ligated into linearized pET21a.

The polynucleotide encoding the polypeptide of the invention, such as, but not limited to the polynucleotide encoding human Semaphorin 3A (SEQ ID NO:2), may be incorporated into a wide variety of expression vectors, which may be transformed into in a wide variety of host cells.

Introduction of a polynucleotide into the host cell can be effected by well-known methods, such as chemical transformation (e.g. calcium chloride treatment), electroporation, conjugation, transduction, calcium phosphate transfection, DEAE-dextran mediated transfection, transvection, microinjection, cationic lipid-mediated transfection, scrape loading, ballistic introduction and infection.

Representative, non-limiting examples of appropriate hosts include bacterial cells, such as cells of *E. coli* and *Bacillus subtilis*.

The polypeptides may be expressed in any vector suitable for expression. The appropriate vector is determined according to the selected host cell. Vectors for expressing proteins in *E. coli*, for example, include, but are not limited to, pET, pK233, pT7 and lambda pSKF. Other expression vector systems are based on betagalactosidase (pEX); maltose binding protein (pMAL); and glutathione S-transferase (pGST).

The polypeptides may be designed to include a protein tag, for example, a His-Tag (six consecutive histidine residues), which can be isolated and purified by conventional methods.

Selection of a host cell transformed with the desired vector may be accomplished using standard selection protocols involving growth in a selection medium which is toxic to non-transformed cells. For example, in the case of *E. coli*, it may be grown in a medium containing an antibiotic selection agent; cells transformed with the expression vector which further provides an antibiotic resistance gene, will grow in the selection medium.

Upon transformation of a suitable host cell, and propagation under conditions appropriate for protein expression, the polypeptide may be identified in cell extracts of the transformed cells. Transformed hosts expressing the polypeptide may be identified by analyzing the proteins expressed by the host, for example, using SDS-PAGE and comparing the gel to an SDS-PAGE gel obtained from the host which was transformed with the same vector but not containing a nucleic acid sequence encoding the desired polypeptide.

The desired polypeptides which have been identified in cell extracts may be isolated and purified by conventional methods, including ammonium sulfate or ethanol precipitation, acid extraction, salt fractionation, ion exchange chromatography, hydrophobic interaction chromatography, gel permeation chromatography, affinity chromatography, and combinations thereof. The polypeptides of the invention may be produced as fusion proteins, attached to an affinity purification protein tag, such as a His-tag, in order to facilitate their rapid purification.

The isolated polypeptide may be analyzed for its various properties, for example specific activity, using methods known in the art. In a non-limiting example, isolated Semaphorin 3A may be analyzed for its ability to reduce expression of Toll Like Receptor 9 (TLR-9) on memory $CD19^+$/$CD27^+$ B cells isolated from SLE patients.

Conditions for carrying out the aforementioned procedures as well as other useful methods are readily determined by those of ordinary skill in the art (see for example, Current Protocols in Protein Science, 1995 John Wiley & Sons).

A non-limiting example of recombinant production of Semaphorin3A is disclosed by Kigel et al. (Kigel B. et al., 2008, PLoS ONE, 3(9): e3287).

Synthetic Production:

Semaphorin 3A according to the present invention may also be produced by synthetic means using well known techniques, such as solid phase synthesis. Synthetic polypeptides may be produced using commercially available laboratory peptide design and synthesis kits. In addition, a number of available FMOC peptide synthesis systems are available. Assembly of a polypeptide or fragment can be carried out on a solid support using for example, an Applied Biosystems, Inc. Model 431A automated peptide synthesizer. The polypeptides may be made by either direct synthesis or by synthesis of a series of fragments that can be coupled using other known techniques.

Any suitable route of administration to a subject may be used for the composition of the present invention, including but not limited to, topical and systemic routes. According to some embodiments, administering is administering systematically. According to some embodiments, the composition is formulated for systemic administration.

According to another embodiment, administration systemically is through a parenteral route. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to some embodiments, parenteral administration is administration intravenously, intra-arterially, intramuscularly, intraperitoneally, intradermally, intravitreally, or subcutaneously. Each of the abovementioned administration routes represents a separate embodiment of the present invention. According to another embodiment, parenteral administration is performed by bolus injection. According to another embodiment, parenteral administration is performed by continuous infusion.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

According to another embodiment, systemic administration of the composition is through injection. For administration through injection, the composition may be formulated in an aqueous solution, for example in a physiologically compatible buffer including but not limited to Hank's solution, Ringer's solution, or physiological salt buffer. Formulations for injection may be presented in unit dosage forms, for example, in ampoules, or in multi-dose containers with, optionally, an added preservative.

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin, for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration. The term "topical administration", as used herein, refers to administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present invention include, for example, emulsion, mousse, lotion, solution and serum.

According to some embodiments, administration of the composition of the invention to a subject in need thereof is by a route selected from the group consisting of: intravenous, intraarterial, subcutaneous and via direct injection into a tissue or an organ. Each possibility represents a separate embodiment of the present invention. According to certain embodiments, administration may be orally.

According to some embodiments, the method of treating SLE according to the present invention further comprises administering to the subject an additional treatment for SLE other than administration of a pharmaceutical composition comprising isolated Semaphorin 3A. According to some embodiments, treating SLE according to the present invention comprises administration of a pharmaceutical composition comprising isolated Semaphorin 3A and administration of an additional treatment for SLE other than a pharmaceutical composition comprising isolated Semaphorin 3A. According to some embodiments, a treatment for SLE is selected from the group consisting of: a corticosteroid, a cytotoxic drug, a non-steroidal anti-inflammatory drug (NSAID), a disease-modifying anti-rheumatic drug (DMARD), an anti-malarial drug, an immunosuppressive drug, an analgesic, intravenous immunoglobulins and a combination thereof. Each possibility represents a separate embodiment of the present invention. According to some embodiments, an additional treatment for SLE other than a pharmaceutical composition comprising isolated Semaphorin 3A is selected from the group consisting of: a corticosteroid, a cytotoxic drug, a non-steroidal anti-inflammatory drug (NSAID), a disease-modifying anti-rheumatic drug (DMARD), an anti-malarial drug, an immunosuppressive drug, an analgesic, intravenous immunoglobulins and a combination thereof. Each possibility represents a separate embodiment of the present invention. According to some embodiments, the composition of the invention further comprises a drug selected from the group consisting of: a corticosteroid, a cytotoxic drug, a non-steroidal anti-inflammatory drug, a disease-modifying anti-rheumatic drug, an anti-malarial drug, an immunosuppressive drug, an analgesic, immunoglobulins and a combination thereof. Each possibility represents a separate embodiment of the present invention. According to other embodiments, a treatment for SLE is a treatment other than for Lupus Nephritis.

Non-limiting examples of disease-modifying anti-rheumatic drugs (DMARDs) include, but are not limited to: abatacept, adalimumab, azathioprine, chloroquine, hydroxychloroquine, Cyclosporin A, etanercept, golimumab, infliximab, leflunomide, methotrexate, minocycline, rituximab, sulfasalazine, Belimumab and a combination thereof. Each possibility represents a separate embodiment of the present invention.

According to some embodiments, the disease-modifying anti-rheumatic drug (DMARD) is an antimalarial. Non-limiting examples of antimalarial drugs include, but are not limited to: Plaquenil, Quinine, Chloroquine, Amodiaquine, Pyrimethamine, Proguanil, Mefloquine, Atovaquone, Primaquine, Artemisinin, Halofantrine and a combination thereof. Each possibility represents a separate embodiment of the present invention.

Non-limiting examples of cytotixic drugs include, but are not limited to: cyclophosphamide, mycophenolate and a combination thereof. Each possibility represents a separate embodiment of the present invention.

According to some embodiments, a non-steroidal anti-inflammatory drug (NSAID) is selected from the group consisting of: salicylates, propionic acid derivatives, acetic acid derivatives, enolic acid derivatives (Oxicam), fenamic acid derivatives (Fenamates), selective COX-2 inhibitors (Coxibs), sulphonanilides and a combination thereof. Each possibility represents a separate embodiment of the present invention. According to some embodiments, the non-steroidal anti-inflammatory drug (NSAID) is a selective COX-2 inhibitor (Coxibs), such as, but not limited to: Celecoxib, Rofecoxib, Valdecoxib, Parecoxib, Lumiracoxib, Etoricoxib and a combination thereof. Each possibility represents a separate embodiment of the present invention.

According to another aspect, the present invention provides a method for determining efficacy of a treatment for Systemic Lupus Erythematosus in a subject in need thereof, the method comprising: making a first measurement of serum Semaphorin 3A concentration in a subject in need thereof; administering a treatment for Systemic Lupus Erythematosus to the subject; making a second measurement of serum Semaphorin 3A concentration in the subject following the treatment; and comparing the first measurement and the second measurement, wherein an increase in serum Semaphorin 3A concentration from the first to the second measurement is indicative of the treatment being efficacious.

According to some embodiments, the present invention provides a method for determining efficacy of a treatment for Lupus Nephritis in a subject in need thereof, the method comprising: making a first measurement of serum Semaphorin 3A concentration in a subject in need thereof; administering a treatment for Systemic Lupus Erythematosus and/or Lupus Nephritis to the subject; making a second measurement of serum Semaphorin 3A concentration in the subject following the treatment; and comparing the first measurement and the second measurement, wherein an increase in serum Semaphorin 3A concentration from the first to the second measurement is indicative of the treatment being efficacious. Each possibility represents a separate embodiment of the present invention.

According to another aspect, the present invention provides a method for determining efficacy of a treatment for Systemic Lupus Erythematosus in a subject in need thereof, the method comprising: making a first measurement of serum Semaphorin 3A concentration in a subject in need thereof prior to administration of a treatment for Systemic Lupus Erythematosus to the subject; making a second measurement of serum Semaphorin 3A concentration in the subject following the treatment; and comparing the first measurement and the second measurement, wherein an increase in serum Semaphorin 3A concentration from the first to the second measurement is indicative of the treatment being efficacious.

According to some embodiments, the present invention provides a method for determining efficacy of a treatment for Lupus Nephritis in a subject in need thereof, the method comprising: making a first measurement of serum Semaphorin 3A concentration in a subject in need thereof prior to administration of a treatment for Systemic Lupus Erythematosus and/or Lupus Nephritis to the subject; making a second measurement of serum Semaphorin 3A concentration in the subject following the treatment; and comparing the first measurement and the second measurement, wherein an increase in serum Semaphorin 3A concentration from the first to the second measurement is indicative of the treatment being efficacious. Each possibility represents a separate embodiment of the present invention.

The methods for determining efficacy of a treatment according to the present invention are based in part on the unexpected discovery that Semaphorin 3A serum concentration in a subject is inversely correlated to SLE disease activity as measured by SLEDAI value. According to some embodiments, a treatment for SLE leading to an increase in Semaphorin 3A serum concentration in a subject in need thereof, is an efficacious treatment. According to some embodiments, a treatment for SLE and/or Lupus Nephritis leading to an increase in Semaphorin 3A serum concentration in a subject in need thereof, is an efficacious treatment. Each possibility represents a separate embodiment of the present invention. According to some embodiments, a treatment for SLE leading to an increase in Semaphorin 3A serum concentration in a subject in need thereof to at least 50 ng/ml, is an efficacious treatment. According to some embodiments, a treatment for SLE and/or Lupus Nephritis leading to an increase in Semaphorin 3A serum concentration in a subject in need thereof to at least 50 ng/ml, is an efficacious treatment. Each possibility represents a separate embodiment of the present invention.

According to some embodiments, the efficacy of a treatment for SLE is indicated by its ability to induce an increase in Semaphorin 3A serum concentration in a subject in need thereof. According to some embodiments, the efficacy of a treatment for SLE and/or Lupus Nephritis is indicated by its ability to induce an increase in Semaphorin 3A serum concentration in a subject in need thereof. Each possibility represents a separate embodiment of the present invention. According to some embodiments, the efficacy of a treatment for SLE and/or Lupus Nephritis is indicated by its ability to induce an increase in Semaphorin 3A serum concentration to at least 50 ng/ml in a subject in need thereof. Each possibility represents a separate embodiment of the present invention. According to some embodiments, the efficacy of a treatment for SLE and/or Lupus Nephritis is indicated by its ability to induce an increase of at least 10%, preferably 20%, in Semaphorin 3A serum concentration in a subject in need thereof. Each possibility represents a separate embodiment of the present invention. According to some embodiments, the efficacy of a treatment for SLE and/or Lupus Nephritis is indicated by its ability to induce an increase of at least 10% in Semaphorin 3A serum concentration in a subject in need thereof. Each possibility represents a separate embodiment of the present invention. In certain embodiments, the efficacy of a treatment for SLE and/or Lupus Nephritis is indicated by its ability to induce an increase of more than 20% in Semaphorin 3A serum concentration in a subject in need thereof. Each possibility represents a separate embodiment of the present invention. Without wishing to be bound by theory or mechanism, the increase in Semaphorin 3A serum concentration which is indicative of the efficacy of a treatment for SLE and/or Lupus Nephritis is dependent on the specific physiological parameters of each subject. Therefore, Semaphorin 3A serum increase which is indicative of an efficient treatment may be less than 10% or more than 20% according to certain embodiments. Each possibility represents a separate embodiment of the present invention.

According to some embodiments, the efficacy of a treatment for SLE is further indicated by at least one clinical outcome selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, the efficacy of a treatment for SLE is further indicated by a decrease in the Systemic Lupus Erythematosus Disease Activity Index value of the treated subject.

According to some embodiments, the efficacy of a treatment for SLE and/or Lupus Nephritis is further indicated by at least one clinical outcome selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, the efficacy of a treatment for SLE and/or Lupus Nephritis is further indicated by a decrease in the Systemic Lupus Erythematosus Disease Activity Index value of the treated subject. Each possibility represents a separate embodiment of the present invention.

According to some embodiments, an efficacious treatment for SLE and/or Lupus Nephritis is a treatment which ameliorates or prevents at least one symptom of SLE and/or Lupus Nephritis, respectively. Each possibility represents a separate embodiment of the present invention. According to some embodiments, an efficacious treatment for SLE and/or Lupus Nephritis is a treatment that shortens at least one flare period. Each possibility represents a separate embodiment of the present invention.

According to some embodiments, measurement of serum Semaphorin 3A concentration may be performed by any method known in the art. According to some embodiments, measurement of serum Semaphorin 3A is performed on a sample obtained from a subject in need thereof. According to some embodiments, measurement of serum Semaphorin 3A is performed on a serum sample obtained from a subject in need thereof. According to some embodiments, measurement of serum Semaphorin 3A is performed on a blood sample obtained from a subject in need thereof. According to some embodiments, Semaphorin 3A can be detected and quantified by any of a number of methods well known to those of skill in the art for polypeptide detection. These may include, but are not limited to, analytic biochemical methods such as electrophoresis, capillary electrophoresis, high performance liquid chromatography (HPLC), thin layer chromatography (TLC), hyperdiffusion chromatography, mass spectroscopy and the like, or various immunological methods such as, but not limited to, fluid or gel precipitin reactions, immunodiffusion (single or double), immunohistochemistry, affinity chromatography, immunoelectrophoresis, radioimmunoassay (RIA), enzyme-linked immunosorbent assay (ELISA), immunofluorescent assay, Western blotting, and the like. According to some embodiments, measurement of serum Semaphorin 3A concentration is performed using an enzyme-linked immunosorbent assay (ELISA).

According to some embodiments, the first measurement is taken as close as possible prior to the beginning of the SLE/Lupus Nephritis treatment, preferably within a day of the beginning of treatment. Each possibility represents a separate embodiment of the present invention. According to some embodiments, the first measurement is taken at the time of diagnosing a subject with SLE or as close as possible to the time of said diagnosis. Each possibility represents a separate embodiment of the present invention. According to some embodiments, the second measurement is taken following termination of the SLE/Lupus Nephritis treatment. Each possibility represents a separate embodiment of the present invention. According to some embodiments, the second measurement is taken in the course of treatment with the SLE/Lupus Nephritis treatment. Each possibility represents a separate embodiment of the present invention. According to some embodiments, the second measurement is taken at least 1, 2, 3, 4, 5, 6, 7, 14, 21, 30, 60, 90 days after the beginning of treatment with the SLE/Lupus Nephritis treatment. Each possibility represents a separate embodiment of the present invention. According to some embodiments, the second measurement is taken at least a week after the beginning of treatment with the SLE/Lupus Nephritis treatment. Each possibility represents a separate embodiment of the present invention. According to some embodiments, the second measurement is taken at least 1, 2, 3, 4, 5, 6, 7, 14, 21, 30, 60, 90 days following termination of treatment with the SLE/Lupus Nephritis treatment. Each possibility represents a separate embodiment of the present invention. According to some embodiments, the second measurement is taken at least a week following termination of treatment with the SLE/Lupus Nephritis treatment. Each possibility represents a separate embodiment of the present invention.

According to another aspect, the present invention provides a method for prognosis of change in Systemic Lupus Erythematosus disease activity in a subject in need thereof, the method comprising: making a first measurement of serum Semaphorin 3A concentration in a subject in need thereof; making a second measurement of serum Semaphorin 3A concentration in the subject at a later time point than said first measurement; and comparing said first measurement and said second measurement; wherein an increase in serum Semaphorin 3A concentration from the first to the second measurement is indicative of a decrease in disease activity; and wherein a decrease in serum Semaphorin 3A concentration from the first to the second measurement is indicative of an increase in disease activity.

According to some embodiments, a decrease in SLE disease activity is characterized by amelioration of at least one symptom of SLE. According to some embodiments, a decrease in SLE disease activity is characterized by at least one clinical effect selected from the group consisting of: an improvement in renal function, a decrease in anti-dsDNA antibody concentration in the serum, a decrease in anti-Cardiolipin antibody concentration in the serum, an increase in serum concentration of complement factor C3 and an increase in serum concentration of complement factor C4. Each possibility represents a separate embodiment of the present invention. According to some embodiments, a decrease in SLE disease activity is evidenced by a decrease in the value of the Systemic Lupus Erythematosus Disease Activity Index of the subject. According to some embodiments, a decrease in disease activity, as indicated by an increase in Semaphorin 3A serum concentration, is indicative of the ending and/or clinical improvement of a flare period. Each possibility represents a separate embodiment of the present invention.

According to some embodiments, an increase in SLE disease activity is characterized by worsening of at least one symptom of SLE. According to some embodiments, an increase in SLE disease activity is characterized by at least one clinical effect selected from the group consisting of: deterioration in renal function, an increase in anti-dsDNA antibody concentration in the serum, an increase in anti-Cardiolipin antibody concentration in the serum, a decrease in serum concentration of complement factor C3 and a decrease in serum concentration of complement factor C4. Each possibility represents a separate embodiment of the present invention. According to some embodiments, an increase in SLE disease activity is evidenced by an increase in the value of the Systemic Lupus Erythematosus Disease Activity Index of the subject. According to some embodiments, an increase in disease activity, as indicated by a decrease in Semaphorin 3A serum concentration, is indicative of the beginning and/or worsening of a flare period. Each possibility represents a separate embodiment of the present invention.

According to some embodiments, serum Semaphorin 3A concentration is inversely correlated to SLE disease activity. According to some embodiments, serum Semaphorin 3A concentration is inversely correlated to SLEDAI value. According to some embodiments, the present invention provides a method for prognosis of lupus nephritis in a subject afflicted with SLE, the method comprising measuring serum Semaphorin 3A concentration in the subject, wherein a concentration up to 50 ng/ml is indicative of Lupus Nephritis in the subject. According to some embodiments, a measurement of serum Semaphorin 3A of up to 50 ng/ml is indicative of Lupus Nephritis. According to some embodiments, a measurement of serum Semaphorin 3A of up to 50 ng/ml is indicative of the presence of serum anti-cardiolipin antibodies.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

EXAMPLES

Example 1: Correlation Between Presence and Severity of SLE and Sema3A Serum Concentration Serum samples from 32 SLE patients, 24 rheumatoid arthritis (RA) patients (disease control) and 40 healthy controls, were all analyzed for Sema3A serum level. SLE patients were evaluated for disease activity by using the Systemic Lupus Erythematosus Disease Activity Index (SLEDAI). All SLE patients were scored mild to severe with a SLEDAI value ranging between 4 and 24. Of relevance, blood was drawn before any steroid pulse or increase of cytotoxic therapy was initiated when severity of disease activity required it.

Table 1 summarizes the clinical and laboratory characteristics of all SLE patients included in this study: SLEDAI value, Sema 3A concentration (ng/ml), presence of anti-cardiolipin antibodies (a.Cal), Lupus Nephritis (LN), presence of anti-dsDNA antibodies (a. dsDNA), low (L) or normal (N) levels of complement C3 and C4, and treatment with various drugs. Seven patients with mild disease were treated only with hydroxychloroquine (HCQ), another eight patients were treated with add-on 2.5 to 5 mg of prednisone, and 17 patients, considered having moderate to severe disease, received low to moderate daily doses of cytotoxic therapy. Nine patients suffered from renal involvement, 19 patients were anti-ds DNA antibody positive and 17 had anti-cardiolipin antibodies of moderate to high titers.

The measurement of Sema3A serum level was conducted using a commercial ELISA kit (USCNK Life Science, Wuhan, P.R. China) according to the manufacturer instructions. The serum samples were stored at $-20°$ until ELISA evaluation. Results of the SLE patients' serum Sema3A levels were correlated with their SLEDAI score, renal involvement and laboratory serologic studies including anti-dsDNA anti-cardiolipin antibodies and C3-C4 serum levels.

Figure 2A:
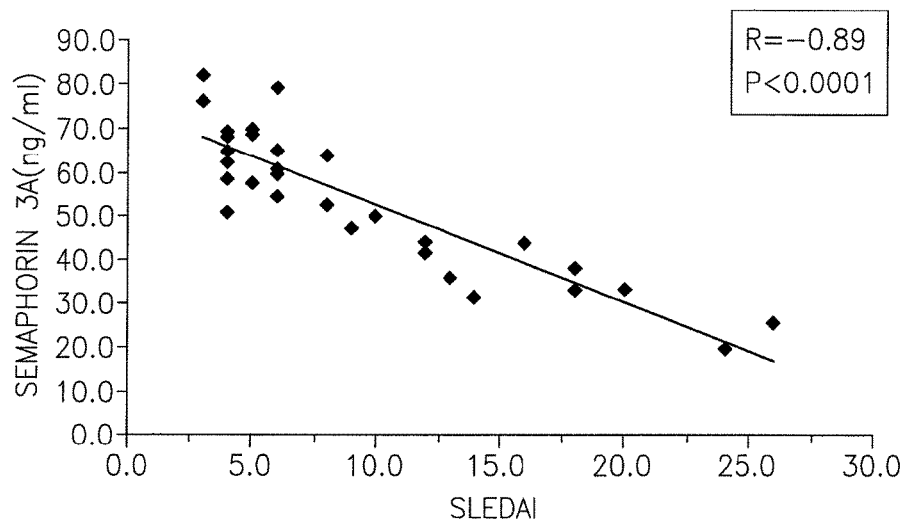
FIGS. 2(A-C) depicts (A) a dot plot demonstrating the negative correlation between Sema3A serum concentration and the SLEDAI value in SLE patients, (B) bar graphs comparing the percentages of SLE patients having kidney involvement (LN+) or not having kidney involvement (LN−) amongst patients having less than 50 ng/ml serum Sema3A (Semaphorin 3A<50%) and patients having more than 50 ng/ml serum Sema3A (Semaphorin 3A>50%), and (C) bar graphs comparing the percentages of SLE patients having anti-cardiolipin antibodies (anti-cardiolipin+) or not having anti-cardiolipin antibodies (anti-cardiolipin−) amongst patients having less than 50 ng/ml serum Sema3A (Semaphorin 3A<50%) and patients having more than 50 ng/ml serum Sema3A (Semaphorin 3A>50%).
Figure 2B:
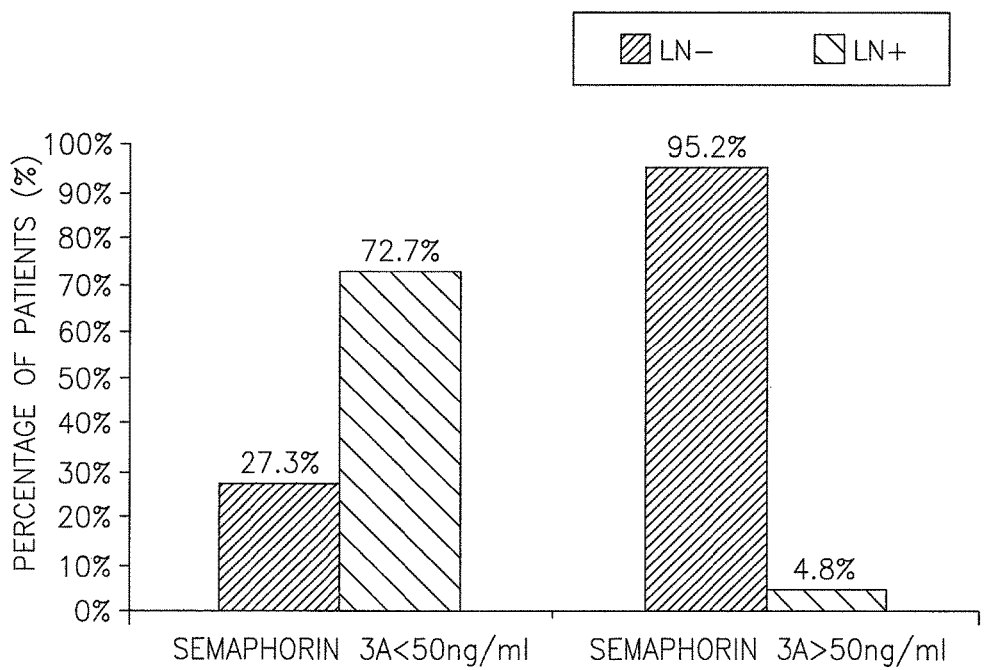
Figure 2C:
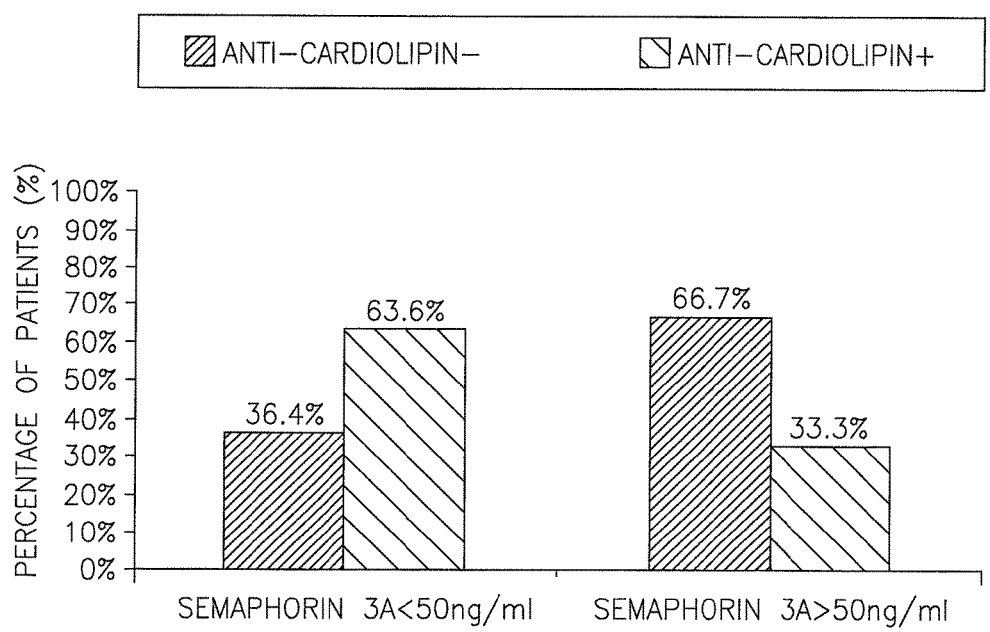
Figure 3A:
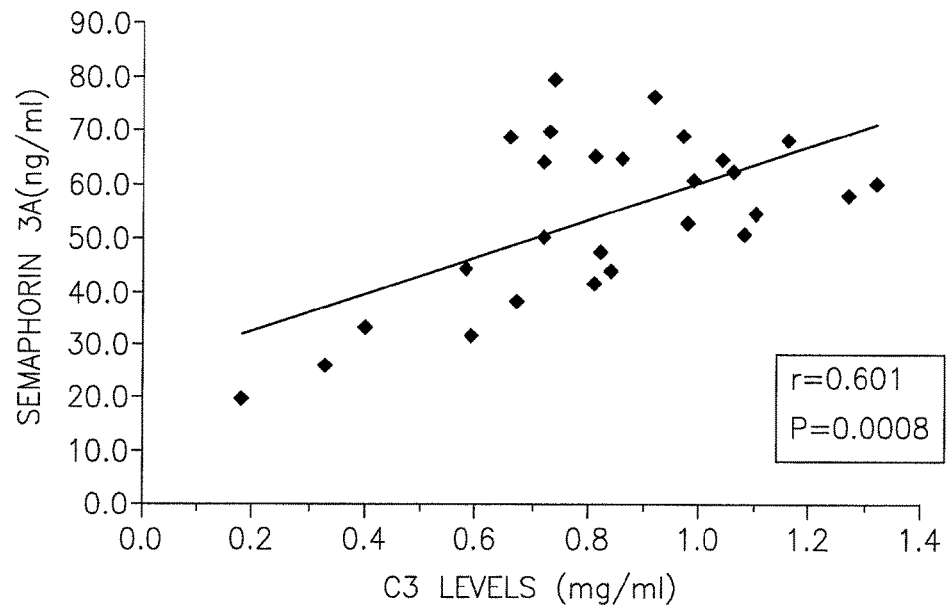
FIGS. 3(A-B) are dot plots demonstrating the positive correlation between serum Sema3A concentration (ng/ml) in SLE patients and complement C3 (A) or C4 (B) levels (mg/ml).
Figure 3B:
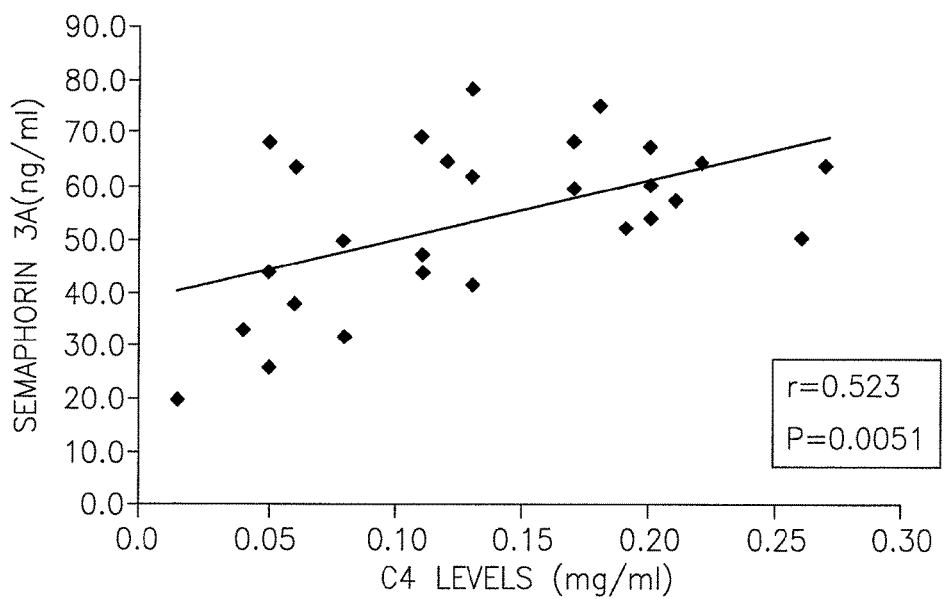

As can be seen in FIG. 1, Sema 3A serum concentration in SLE patients (55.04±16.30 ng/ml) was significantly lower than that of control subjects (74.41±17.60 ng/ml, P<0.0001). As can be seen in FIG. 2A, Sema 3A serum concentration was found to be inversely correlated with disease activity of SLE patients as represented by SLEDAI values (R=−0.89, P<0.0001). Moreover, as can be seen in FIG. 2B, 73% of SLE patients which had a Sema3A serum concentration below 50 ng/ml showed kidney involvement (Lupus Nephritis) as compared to only 5% of patients having Sema3A serum concentration above 50 ng/ml. FIG. 2C further demonstrates that 64% of SLE patients which had a Sema3A serum concentration below 50 ng/ml were positive for anti-cardiolipin antibodies as compared to only 33% of patients having Sema3A serum concentration above 50 ng/ml. In addition, a positive correlation was found between the serum level of Sema3A and both C3 values (r=0.078, P=0.0008) and C4 values (r=0.523, P=0.005) (FIGS. 3A and 3B, respectively).

Example 2: Expression of Sema3A and NP-1 on B-Cells from Healthy Subjects and SLE Patients Flow cytometry was used in order to compare Sema3A or NP-1 expression in $CD19^+CD25^{high}$ B cells of healthy subjects vs. SLE patients. Briefly, whole blood samples were stained with human anti-CD19 FITC/P antibody and human anti-CD25 PC5 antibody (Immunotech, Beckman-Coulter, Marsellie, France). The blood samples were further stained with either human anti-sema3A AlexaFluor 488 antibody or human anti-NP1 PE antibody (R&D, Minneapolis, Minn., USA). The stained cells were then evaluated using a Flow Cytometer (FC500 and CXP software, Beckman Coulter, Brea, Calif., USA).

Figure 4:
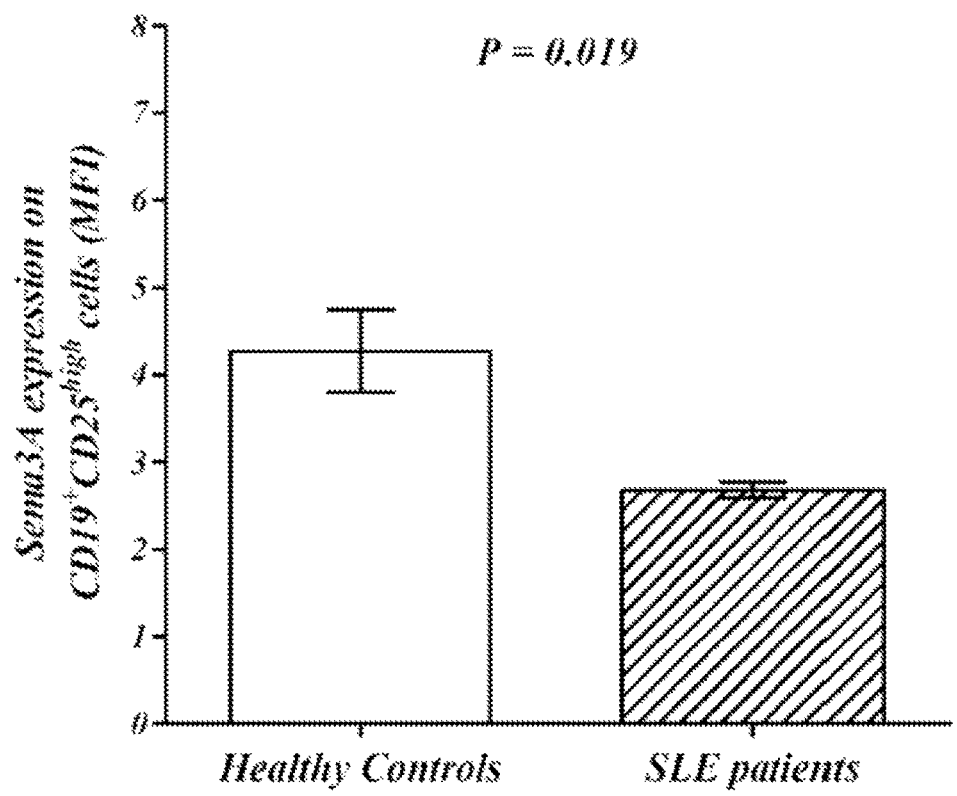
FIG. 4 depicts a bar graph comparing Sema3A expression on $CD19^+CD25^{high}$ B-Cells obtained from SLE patients and healthy controls, as evaluated by Mean Fluorescent Intensity (MFI).

Significantly less Sema3A had been expressed on $CD19^+ CD25^{high}$ B cells derived from SLE patients than on cells derived from healthy controls (52.2±5.8% versus 82.6±6.4% respectively, P<0.0001). FIG. 4 presents Sema 3A levels as Mean Fluorescent Intensity (MFI) values of samples from SLE patients vs. healthy subjects (2.68±0.09 versus 4.27±0.47 respectively, P=0.019).

NP-1 expression was also found to be significantly lower on examined cells from SLE patients when compared to cells from healthy individuals (10.8±3.6% versus 15.4±1.4% respectively, P=0.03).

TABLE 1

Clinical characteristics of SLE patients

| Patient | SLEDAI | Sema3A (ng/ml) | a. Cal | a. LN | dsDNA | Complement C3 | C4 | Treatment |
|---|---|---|---|---|---|---|---|---|
| 1 | 16 | 44 |  | + | + | L | L | HCQ; P |
| 2 | 14 | 32 | + | + | + | L | L | HCQ; P |
| 3 | 3 | 82 |  |  |  | N | N | HCQ |
| 4 | 4 | 63 |  |  |  | N | L | P |
| 5 | 4 | 69 | + |  |  | N | N | HCQ; P; AZA |
| 6 | 4 | 51 | + |  |  | N | N | HCQ; Atabrin |
| 7 | 5 | 69 |  |  | + | N | L | HCQ; P |
| 8 | 8 | 53 |  |  |  | N | L | HCQ; P; AZA |
| 9 | 6 | 79 | + |  | + | L | L | HCQ; P; AZA |
| 10 | 12 | 44 |  |  |  | N | L | HCQ; P; AZA |
| 11 | 6 | 65 |  |  |  | N | N | HCQ; P |
| 12 | 9 | 48 |  |  | + | N | L | HCQ; P; AZA |
| 13 | 6 | 65 | + |  | + | L | L | HCQ; P; AZA |
| 14 | 3 | 76 |  |  |  | N | L | HCQ; P |
| 15 | 12 | 42 | + |  | + | N | L | HCQ; P; AZA |
| 16 | 8 | 64 | + |  | + | L | L | HCQ; P; |
| 17 | 18 | 38 | + | + | + | L | L | HCQ; P; AZA |
| 18 | 18 | 33 | + | + | + | L | L | HCQ; P; MTX; IVIg |
| 19 | 4 | 68 |  |  | + | N | L | HCQ; P; AZA |
| 20 | 6 | 55 |  |  |  | N | N | HCQ; P |
| 21 | 6 | 60 | + |  | + | N | L | HCQ; P |
| 22 | 24 | 20 | + | + | + | L | L | HCQ; P; MTX; IVIg |
| 23 | 5 | 70 | + |  |  | N | N | HCQ; P |
| 24 | 10 | 50 | + | + | + | L | L | HCQ; P; AZA |
| 25 | 13 | 36 | + | + | + | L | L | HCQ; P; |
| 26 | 4 | 65 |  |  | + | N | N | HCQ; |
| 27 | 26 | 26 | + | + | + | L | L | HCQ; P; CYC |
| 28 | 6 | 61 |  |  |  | N | N | HCQ; P; AZA |
| 29 | 4 | 63 |  |  |  | N | N | HCQ; P; AZA |
| 30 | 4 | 59 |  |  |  | N | L | HCQ |
| 31 | 5 | 58 | + |  | + | N | N | HCQ; P; AZA |
| 32 | 20 | 34 | + | + | + | L | L | HCQ; P; CYC | a. Cal, anti-cardiolipin;
a. dsDNA, anti-double-stranded DNA;
AZA, azathioprine;
CYC, cyclophosphamide;
F, female;
HCQ, hydroxychloroquine;
IVIg, intravenous immunoglobulin;
L, low;
LN, lupus nephritis;
M, male;
MTX, Methotrexate;
N, normal;
P, prednisone;
Sema3A, semaphorin 3A.

Example 3: Expression of Toll-Like Receptor 9 on B-Cells from SLE Patients Incubated with Sema3A Conditioned Media In order to examine the effect of treatment with Sema3A on the expression of Toll-Like Receptor 9 (TLR-9) on B cells of SLE patients, B cells were purified from peripheral blood of SLE patients. Briefly, peripheral blood mononuclear cells (PBMCs) were isolated on Lymphoprep (Axis-Shield, Oslo, Norway), and B lymphocytes were isolated by positive selection using the CD22 microbeads (20 µl/$10^7$ cells; Miltenyi Biotec, Bergisch Gladbach, Germany) according to the manufacturer's instructions, achieving >98% purity. Next, Purified B cells, gating on memory CD19+/CD27+ B cells (Immunotech, Beckman-Coulter, Marseile, France) from SLE patients were analyzed for TLR-9 expression:

Purified B cells from each patient, activated by cytosine-phosphodiester-guanine oligodeoxynucleotides (ODN-CpG), were incubated for 60 hours with conditioned media from HEK293-cells infected by NSPI-CMV-FLAG lentivirus with or without sema3A cDNA, as previously described (Bombardier C. et al., 1992, Arthritis Rheum., 35:630-640). Accordingly, conditioned medium from HEK293 cells infected by NSPI-CMV-FLAG lentivirus with Sema3A cDNA contained FLAG-tagged Sema3A, as set forth in SEQ ID NO:3.

Following incubation, cells were fixed and permeabilized using a commercial kit according to the manufacturer's instructions ('Fix and Perm', Invitrogen, Carlsbad, Calif., USA) and analyzed for TLR-9 expression. Staining was performed using a specific monoclonal anti-human TLR-9-PE antibody (Imgenex, San Diego, Calif., USA) and evaluated using a FC500 flow cytometer.

Figure 5:
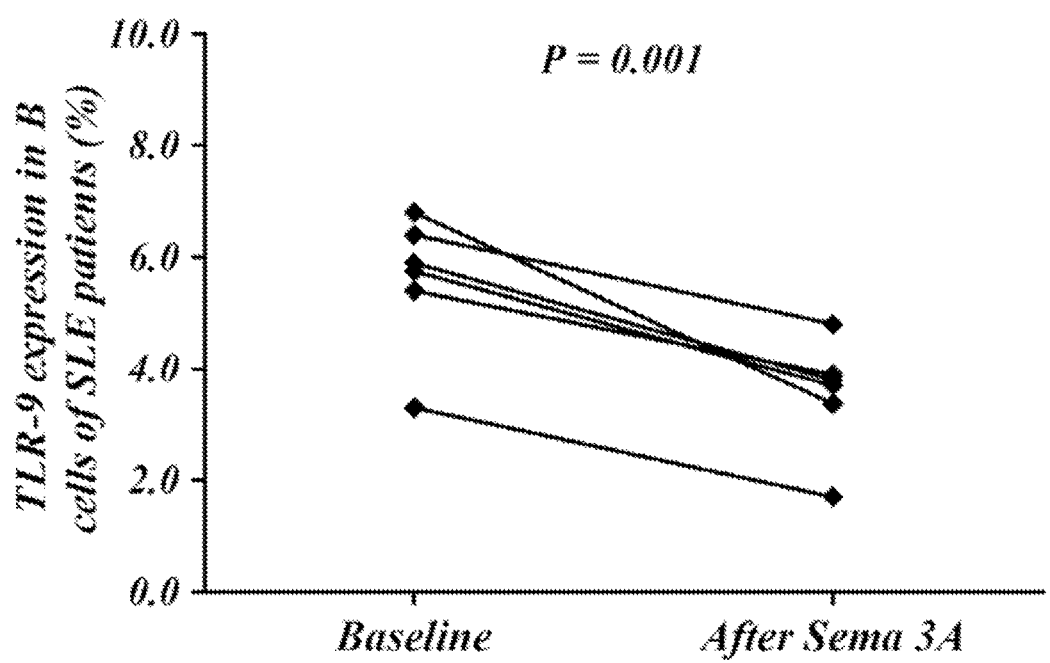
FIG. 5 shows a dot plot comparing the percentage of Toll-Like-Receptor 9 (TLR-9) expressing B cells out of B cells that were isolated from SLE patients and treated either with Sema3A containing medium (denoted as "After Sema3A") or cell culture medium (denoted as "Baseline").

Next, the percentage of cells expressing TLR-9 following incubation with the Sema3A-containing media or the control culture media was compared. FIG. 5 demonstrates that TLR-9 expression on memory B cells was lower following incubation of the cells with Sema3A ("After Sema3A") by almost 50% (P=0.001) as compared to expression on cells incubated with medium alone ("Baseline"). Each line in FIG. 5 represents the difference in TLR-9 expression between cells from a single subject that were either incubated with control or Sema 3A containing medium.

Example 4: Examining the Effect of Semaphorin 3A Administration in NZB/NZW F1 Mice In order to assess how Semaphorin 3A affects SLE disease progression in NZB/NZW F1 mice (serving as a model system for SLE), mice are divided into 4 groups:

Prevention Group:

In this group, 5 mice are injected with recombinant Sema3A on a daily basis and 5 mice are injected with PBS, as a control group. Mice are injected from the age of 6 weeks for 90 days. During this period, both groups are assessed for the development of auto-antibodies (e.g. anti-dsDNA and anti-cardiolipin), kidney function tests (creatinine and BUN), complete blood count on weekly basis and detection of early proteinuria. In addition clinical status of the mice is evaluated by assessing their weight. After this period, the mice are sacrificed and a histological evaluation of their kidneys is performed.

Treatment Group:

In this group, 5 mice are injected with recombinant Sema3A on a daily basis and 5 mice are injected with PBS, as a control group. Mice are injected from the onset of clinical and laboratory signs of SLE (at four month of age with early proteinuria) and continue for 90 days. During this period, both groups are assessed for the development of auto-antibodies (e.g. anti-dsDNA and anti-cardiolipin), kidney function tests (creatinine and BUN), complete blood count on weekly basis and detection of early proteinuria. In addition clinical status of the mice is evaluated by assessing their weight. After this period, the mice are sacrificed and a histological evaluation of their kidneys is performed.

Example 5: Comparison of Semaphorin 3A Expression on $CD19^+CD25^{high}$ B-Cells and $CD19^+CD25^{low}$ B-Cells Flow cytometry was used in order to compare Sema3A expression between $CD19^+CD25^{high}$ and $CD19^+CD25^{low}$ B cells purified from peripheral blood of SLE patients. Peripheral blood mononuclear cells (PBMCs) were isolated on Lymphoprep (Axis-Shield, Oslo, Norway) from peripheral blood of SLE patients, and B lymphocytes were isolated by positive selection using the CD22 microbeads (20 µl/$10^7$ cells; Miltenyi Biotec, Bergisch Gladbach, Germany) according to the manufacturer's instructions. The purified B cells were stained with monoclonal antibodies: human anti-CD19 FITC/PE and CD25 PC5 (Immunotech, Beckman-Coulter, Marsellie, France), and human anti-sema3A AlexaFluor 488 (R&D, Minneapolis, Minn., USA), and evaluated in Flow cytometry software (FC500 and CXP software, Beckman Coulter, Brea, Calif., USA).

FIGS. 6A and 6B show the same flow cytometry scatter, plotting CD19 positive cells vs. CD25 positive cells. FIG. 6A shows the cell range used to examine Sema3A expression on $CD19^- CD25^{low}$ cells and $CD19^+CD25^{low}$ B cells. FIG. 6B shows the cell range used to examine Sema 3A expression on $CD19^+CD25^{high}$ B cells. As can be seen in FIGS. 6C-E, $CD19^-CD25^{low}$ cells showed 2.1% Semaphorin 3A expression (marked Sema3A on CD19-non CD25 cells in FIG. 6C), $CD19^+CD25^{low}$ B cells showed 17% Semaphorin3A expression (marked Sema3A on CD19–CD25 cells in FIG. 6D) and $CD19^+CD25^{high}$ B cells showed 35% Semaphorin 3A expression (marked Sema3A on CD19-CD25 high cells in FIG. 6E).

Example 6: Comparison Between Semaphorin 3A Expression on $CD4/CD25^{high}$ T Regulatory Cells of SLE Patients and Healthy Subjects In order to examine Sema3A expression on $CD4/CD25^{high}$ T regulatory cells, whole blood samples from healthy subjects and SLE patients were stained using the following monoclonal antibodies: human anti-CD4 PE and CD25 PC5 (Immunotech, Beckman-Coulter, Marsellie, France), and human anti-sema3A AlexaFluor 488 (R&D, Minneapolis, Minn., USA). The cells were evaluated using a flow cytometry software (FC500 and CXP software, Beckman Coulter, Brea, Calif., USA). Similar Sema3A expression was observed on $CD4/CD25^{high}$ T regulatory cells from SLE patients and healthy subjects.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. It is to be understood that further trials are being conducted to establish clinical effects.

The invention claimed is:

1. A method for ameliorating symptoms associated with Systemic Lupus Erythematosus in a subject afflicted with Systemic Lupus Erythematosus, the method comprising administering to the subject a pharmaceutical composition comprising a therapeutically effective amount of isolated Semaphorin 3A, or a polynucleotide encoding for Semaphorin 3A, thereby ameliorating the symptoms associated with Systemic Lupus Erythematosus in the subject.

2. The method of claim 1, wherein said ameliorating results in at least one clinical outcome selected from the group consisting of: an improvement in renal function, a decrease in anti-dsDNA antibody concentration in the serum, a decrease in anti-cardiolipin antibody concentration in the serum, an increase in serum concentration of complement factor C3 and an increase in serum concentration of complement factor C4.

3. The method of claim 1, wherein said ameliorating results in a decrease in the Systemic Lupus Erythematosus Disease Activity Index value of said subject.

4. The method of claim 1, wherein administering to a subject in need thereof is by a route selected from the group consisting of: intravenous, intraarterial, subcutaneous and via direct injection into a tissue or an organ.

5. The method of claim 1, wherein said Semaphorin 3A peptide has a sequence as set forth by SEQ ID NO: 1, or is encoded by a polynucleotide having a sequence as set forth by SEQ ID NO: 2.

6. The method of claim 1, wherein said method further comprises administering to said subject an additional treatment for Systemic Lupus Erythematosus.

7. The method of claim 6, wherein said additional treatment is selected from the group consisting of: a corticosteroid, a cytotoxic drug, a non-steroidal anti-inflammatory drug, a disease-modifying anti-rheumatic drug, an anti-malarial drug, an immunosuppressive drug, an analgesic, intravenous immunoglobulins and a combination thereof.

* * * * *